(12) United States Patent
Britovsek et al.

(10) Patent No.: US 6,451,939 B1
(45) Date of Patent: Sep. 17, 2002

(54) POLYMERIZATION CATALYSTS

(75) Inventors: George Johan Peter Britovsek, London (GB); Birgit Angelika Dorer, Mutterstadt (DE); Vernon Charles Gibson, London (GB); Brian Stephen Kimberley, Sunbury (GB); Gregory Adam Solan, Leicester (GB)

(73) Assignee: BP Chemicals Limited, London (GB)

( * ) Notice: Subject to any disclaimer, the term of this patent is extended or adjusted under 35 U.S.C. 154(b) by 0 days.

(21) Appl. No.: 09/520,127

(22) Filed: Mar. 6, 2000

Related U.S. Application Data

(63) Continuation of application No. PCT/GB98/02638, filed on Sep. 2, 1998.

(30) Foreign Application Priority Data

| Date | | Number |
|---|---|---|
| Sep. 5, 1997 | (GB) | 9718775 |
| Oct. 21, 1997 | (GB) | 9722104 |
| Mar. 12, 1998 | (GB) | 9805336 |
| Mar. 20, 1998 | (GB) | 9806106 |
| Mar. 27, 1998 | (GB) | 9806661 |
| May 7, 1998 | (GB) | 9809598 |

(51) Int. Cl.$^7$ .............. C08F 4/60; C08F 4/695; C08F 4/70

(52) U.S. Cl. ........... 526/161; 526/134; 526/169.1; 526/172; 526/171; 526/328; 526/329; 526/328.5; 526/329.3; 526/329.7; 526/346; 502/155; 502/150

(58) Field of Search ............. 526/134, 161, 526/169.1, 172, 171, 328, 329, 328.5, 329.3, 329.7, 346

(56) References Cited

U.S. PATENT DOCUMENTS

| | | | | |
|---|---|---|---|---|
| 5,955,555 A | * | 9/1999 | Bennet | 526/133 |
| 6,150,482 A | * | 11/2000 | Brookhart et al. | 526/161 |
| 6,252,022 B1 | * | 6/2001 | Arthur et al. | 526/172 |

FOREIGN PATENT DOCUMENTS

| | | |
|---|---|---|
| WO | WO 98/27124 | 6/1998 |

OTHER PUBLICATIONS

G.J.P. Britovsek et al., "Novel Olefin Polymerization Catalysts Based on Iron and Cobalt", Chem. Commun., pp.849–850, (1998).

B.L. Small et al., "New Iron and Cobalt Catalysts for the Polymerization of Olefins", Polym. Prepr., vol. 39 (1), p. 213, (1998).

F. Guérin et al., "Ortho–Substituted Aryl Diamido Complexes of Zirconium: Observation of Rotameric Isomers", Polyhedron, vol. 17, No. 5–6, pp. 917–923, (1998).

J.D. Curry et al., "Metal Complexes Derived from Substituted Hydrazones of 2,6–Diacetylpyridine", Inorganic Chemistry, vol. 6, No. 8, pp. 1570–1574, (1967).

A. Bonardi et al., "Copper (II), Nickel (II) and Iron (II) Complexes of 2,6–Diacetylpyridine Bis{[DL–hydroxy(phenyl)acetic]hydrazone}. X–Ray Structure of a 1:2 Metal:Ligand Nickel Complex", Inorganica Chimica Acta, vol 232, No. 1–2, pp. 211–216, (1995).

S. Kazuhiko, "26–Ethylidenenitrilophenylpyridine, Production thereof and Metal Salt Complex", Patent Abstracts of Japan, JP 02 078663, (1990), (Abstract Only).

B.L. Small et al., "Iron–Based Catalysts with Exceptionally High Activities and Selectivities for Oligomerization of Ethylene to Linear α–Olefins", J. Am. Chem. Soc., vol. 120, No. 28, pp. 7143–7144, (1998).

M.J. Blandamer et al., "Solubilities of Salts and Kinetics of Reaction Between Hydroxide Ions and Iron (II)–Di–imine Complexes in Water–Methanol Mixtures", J. Chem. Soc., Faraday Trans. 1, vol. 82, No. 5, pp. 1471–1514, (1986).

* cited by examiner

*Primary Examiner*—David W. Wu
*Assistant Examiner*—R. Rabago
(74) *Attorney, Agent, or Firm*—Finnegan, Henderson, Farabow, Garrett and Dunner, L.L.P.

(57) ABSTRACT

Catalyst systems for the polymerization or copolymerization of 1-olefins which contain nitrogen-containing transition metal compounds comprising the skeletal unit depicted in formula (B),

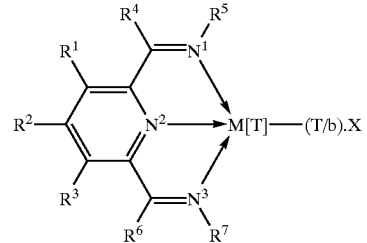

Formula B wherein M is Fe[II] Fe[III], Co[I], Co[II], Co[III], Mn[I], Mn[II], Mn[III], Mn[IV], Ru[II], Ru[III] or Ru[IV]; X is an atom or group covalently or ionically bonded to the transition metal M; T is the oxidation state of the transition metal M and b is the valency of the atom or group X; and $R^1$–$R^7$ are independently selected from hydrogen, halogen, hydrocarbyl, substituted hydrocarbyl, heterohydrocarbyl or substituted heterohydrocarbyl.

34 Claims, No Drawings

POLYMERIZATION CATALYSTS

This application is a continuation of International Application No. PCT/GB98/02638, filed Sep. 2, 1998, the content of which is incorporated herein by reference.

The present invention relates to transition metal-based polymerisation catalysts and to their use in the polymerisation and copolymerisation of olefins.

The use of certain transition metal compounds to polymerise 1-olefins, for example, ethylene, is well established in the prior art. The use of Ziegler-Natta catalysts, for example, those catalysts produced by activating titanium halides with organometallic compounds such as triethylaluminium, is fundamental to many commercial processes for manufacturing polyolefins. Over the last twenty or thirty years, advances in the technology have led to the development of Ziegler-Natta catalysts which have such high activities that olefin polymers and copolymers containing very low concentrations of residual catalyst can be produced directly in commercial polymerisation processes. The quantities of residual catalyst remaining in the produced polymer are so small as to render unnecessary their separation and removal for most commercial applications. Such processes can be operated by polymerising the monomers in the gas phase, or in solution or in suspension in a liquid hydrocarbon diluent. Polymerisation of the monomers can be carried out in the gas phase (the "gas phase process"), for example by fluidising under polymerisation conditions a bed comprising the target polyolefin powder and particles of the desired catalyst using a fluidising gas stream comprising the gaseous monomer. In the so-called "solution process" the (co)polymerisation is conducted by introducing the monomer into a solution or suspension of the catalyst in a liquid hydrocarbon diluent under conditions of temperature and pressure such that the produced polyolefin forms as a solution in the hydrocarbon diluent. In the "slurry process" the temperature, pressure and choice of diluent are such that the produced polymer forms as a suspension in the liquid hydrocarbon diluent. These processes are generally operated at relatively low pressures (for example 10–50 bar) and low temperature (for example 50 to 150° C.).

Commodity polyethylenes are commercially produced in a variety of different types and grades. Homopolymerisation of ethylene with transition metal based catalysts leads to the production of so-called "high density" grades of polyethylene. These polymers have relatively high stiffness and are useful for making articles where inherent rigidity is required. Copolymerisation of ethylene with higher 1-olefins (eg butene, hexene or octene) is employed commercially to provide a wide variety of copolymers differing in density and in other important physical properties. Particularly important copolymers made by copolymerising ethylene with higher 1-olefins using transition metal based catalysts are the copolymers having a density in the range of 0.91 to 0.93. These copolymers which are generally referred to in the art as "linear low density polyethylene" are in many respects similar to the so called "low density" polyethylene produced by the high pressure free radical catalysed polymerisation of ethylene. Such polymers and copolymers are used extensively in the manufacture of flexible blown film.

In recent years the use of certain metallocene catalysts (for example biscyclopentadienylzirconiumdichloride activated with alumoxane) has provided catalysts with potentially high activity. However, metallocene catalysts of this type suffer from a number of disadvantages, for example, high sensitivity to impurities when used with commercially available monomers, diluents and process gas streams, the need to use large quantities of expensive alumoxanes to achieve high activity, and difficulties in putting the catalyst on to a suitable support.

Patent Application WO98/27124 published on Jun. 25, 1998 discloses that ethylene may be polymerised by contacting it with certain iron or cobalt complexes of selected 2,6-pyridinecarboxaldehydebis(imines) and 2,6-diacylpyridinebis(imines).

An object of the present invention is to provide a novel catalyst suitable for polymerising monomers, for example, olefins, and especially for polymerising ethylene alone or for copolymerising ethylene with higher 1-olefins. A further object of the invention is to provide an improved process for the polymerisation of olefins, especially of ethylene alone or the copolymerisation of ethylene with higher 1-olefins to provide homopolymers and copolymers having controllable molecular weights. For example, using the catalysts of the present invention there can be made a wide variety of polyolefins such as, for example, liquid polyolefins, oligomers, resinous or tacky polyolefins, solid polyolefins suitable for making flexible film and solid polyolefins having high stiffness.

The present invention provides a polymerisation catalyst comprising (1) a nitrogen-containing transition metal compound having the following Formula B, and (2) an activating quantity of an activator compound selected from organoaluminium compounds and hydrocarbylboron compounds,

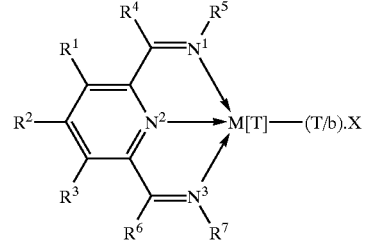

Formula B wherein M[T] is Fe[II], Fe[III], Co[I], Co[II], Co[III], Ru[II], Ru[III], Ru[IV], Mn[I], Mn[II], Mn[III] or Mn[IV]; X represents an atom or group covalently or ionieally bonded to the transition metal M; T is the oxidation state of the transition metal M and b is the valency of the atom or group X; $R^1$, $R^2$, $R^3$, $R^4$, and $R^6$ are independently selected from hydrogen, halogen, hydrocarbyl, substituted hydrocarbyl, heterohydrocarbyl or substituted heterohydrocarbyl;

and such that (1)

when M is Fe, Co or Ru, $R^5$ and $R^7$ are independently selected from hydrogen, halogen, hydrocarbyl, substituted hydrocarbyl, heterohydrocarbyl or substituted heterohydrocarbyl; and when any two or more of $R^1$–$R^7$ are hydrocarbyl, substituted hydrocarbyl, heterohydrocarbyl or substituted heterohydrocarbyl, said two or more can be linked to form one or more cyclic substituents, or such that (2)

when M is Fe, Co, Mn or Ru, then $R^5$ is represented by the group "P" and $R^7$ is represented by the group "Q" as follows:

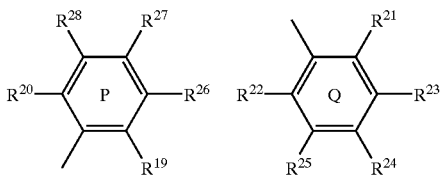

wherein $R^{19}$ to $R^{28}$ are independently selected from hydrogen, halogen, hydrocarbyl, substituted hydrocarbyl, heterohydrocarbyl or substituted heterohydrocarbyl; when any two or more of $R^1$ to $R^4$, $R^6$ and $R^{19}$ to $R^{28}$ are hydrocarbyl, substituted hydrocarbyl, heterohydrocarbyl or substituted heterohydrocarbyl, said two or more can be linked to form one or more cyclic substituents; with the proviso that at least one of $R^{19}$, $R^{20}$, $R^{21}$ and $R^{22}$ is hydrocarbyl, substituted hydrocarbyl, heterohydrocarbyl or substituted heterohydrocarbyl when neither of the ring systems P and Q forms part of a polyaromatic fused-ring system, or such that (3)

when M is Fe, Co, Mn or Ru, then $R^1$ is a group having the formula —$NR^{29}R^{30}$ and $R^7$ is a group having the formula —$NR^{31}R^{32}$, wherein $R^{29}$ to $R^{32}$ are independently selected from hydrogen, halogen, hydrocarbyl, substituted hydrocarbyl, heterohydrocarbyl or substituted heterohydrocarbyl; when any two or more of $R^1$ to $R^4$, $R^6$ and $R^{29}$ to $R^{32}$ are hydrocarbyl, substituted hydrocarbyl, heterohydrocarbyl or substituted heterohydrocarbyl, said two or more can be linked to form one or more cyclic substituents.

Thus, one embodiment of the present invention provides a polymerisation catalyst comprising (1) a nitrogen-containing transition metal compound comprising the skeletal unit depicted in Formula B and
(2) an activating quantity of an activator compound selected from organoaluminium compounds and hydrocarbylboron compounds, Formula B

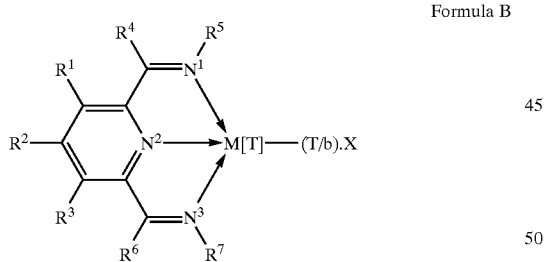

wherein M is Fe[II], Fe[III], Ru[II], Ru[III] or Ru[IV]; X represents an atom or group covalently or ionically bonded to the transition metal M; T is the oxidation state of the transition metal M and b is the valency of the atom or group X; $R^1$, $R^2$, $R^3$, $R^4$ and $R^6$ are independently selected from hydrogen, halogen, hydrocarbyl, substituted hydrocarbyl, heterohydrocarbyl or substituted heterohydrocarbyl; $R^5$ and $R^7$ are independently selected from hydrogen, halogen, hydrocarbyl, substituted hydrocarbyl, heterohydrocarbyl or substituted heterohydrocarbyl.

When any two or more of $R^1$–$R^7$ are hydrocarbyl, substituted hydrocarbyl, heterohydrocarbyl or substituted heterohydrocarbyl, said two or more can be linked to form one or more cyclic substituents.

A further embodiment of the present invention provides a polymerisation catalyst comprising (1) a nitrogen-containing transition metal compound of Formula Z and
(2) an activating quantity of an activator compound selected from organoaluminium compounds and hydrocarbylboron compounds, Formula Z

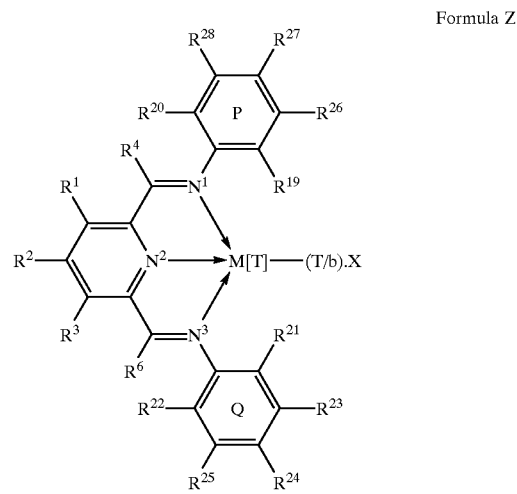

wherein M is Fe[II], Fe[III], Co[I], Co[II], Co[III], Mn[I], Mn[II], Mn[III], Mn[IV], Ru[II], Ru[III] or Ru[IV]; X represents an atom or group covalently or ionically bonded to the transition metal M; T is the oxidation state of the transition metal M and b is the valency of the atom or group X; $R^1$ to $R^4$, $R^6$ and $R^{19}$ to $R^{28}$ are independently selected from hydrogen, halogen, hydrocarbyl, substituted hydrocarbyl, heterohydrocarbyl or substituted heterohydrocarbyl; when any two or more of $R^1$ to $R^4$, $R^6$ and $R^{19}$ to $R^{28}$ are hydrocarbyl, substituted hydrocarbyl, heterohydrocarbyl or substituted heterohydrocarbyl, said two or more can be linked to form one or more cyclic substituents; with the proviso that at least one of $R^{19}$, $R^{20}$, $R^{21}$ and $R^{22}$ is hydrocarbyl, substituted hydrocarbyl, heterohydrocarbyl or substituted heterohydrocarbyl when neither of the ring systems P and Q forms part of a polyaromatic fused-ring system. In this particular aspect of the present invention, in the case that neither of the ring systems P and Q forms part of a polyaromatic ring system, it is preferred that at least one of $R^{19}$ and $R^{20}$, and at least one of $R^{21}$ and $R^{22}$ is selected from hydrocarbyl, substituted hydrocarbyl, heterohydrocarbyl or substituted heterohydrocarbyl. In one embodiment of the present invention, $R^{19}$, $R^{20}$, $R^{21}$ and $R^{22}$ are hydrocarbyl, substituted hydrocarbyl, heterohydrocarbyl or substituted heterohydrocarbyl when neither of the ring systems P and Q forms part of a polyaromatic fused-ring system.

Subject to the foregoing provisos regarding $R^{19}$, $R^{20}$, $R^{21}$ and $R^{22}$ in Formula Z, $R^1$ to $R^4$, $R^6$ and $R^{19}$ to $R^{28}$ in the compounds depicted in Formulae B and Z of the present invention are preferably independently selected from hydrogen and $C_1$ to $C_8$ hydrocarbyl, for example, methyl, ethyl, n-propyl, n-butyl, n-hexyl, and n-octyl. In Formula B, $R^5$ and $R^7$ are preferably independently selected from substituted or unsubstituted alicyclic, heterocyclic or aromatic groups, for example, phenyl, 1-naphthyl, 2-naphthyl, 2-methylphenyl, 2-ethylphenyl, 2,6-diisopropylphenyl, 2,3- diisopropylphenyl, 2,4-diisopropylphenyl, 2,6-di-n-butylphenyl, 2,6-dimethylphenyl, 2,3-dimethylphenyl, 2,4-dimethylphenyl, 2-t-butylphenyl, 2,6-diphenylphenyl, 2,4,6-trimethylphenyl, 2,6-trifluoromethylphenyl, 4-bromo-2,6-dimethylphenyl, 3,5 dichloro2,6-diethylphenyl, and 2,6,bis (2,6-dimethylphenyl)phenyl, cyclohexyl and pyridinyl.

The ring systems P and Q in Formula Z are preferably independently 2,6-hydrocarbylphenyl or fused-ring polyaromatic, for example, 1-naphthyl, 2-naphthyl, 1-phenanthrenyl and 8-quinolinyl.

Another embodiment of the present invention provides a polymerisation catalyst comprising
(1) a nitrogen-containing transition metal compound of Formula T and
(2) an activating quantity of an activator compound selected from organoaluminium compounds and hydrocarbylboron compounds,

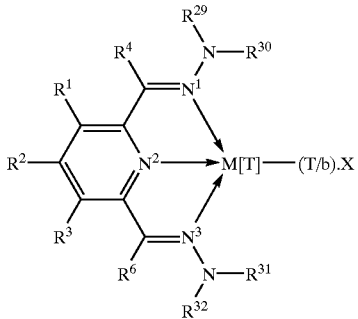

Formula T wherein M is Fe[II], Fe[III], Co[I], Co[II], Co[III], Mn[I], Mn[II], Mn[III], Mn[IV], Ru[II], Ru[III] or Ru[IV]; X represents an atom or group covalently or ionically bonded to the transition metal M; T is the oxidation state of the transition metal M and b is the valency of the atom or group X; $R^1$ to $R^4$, $R^6$ and $R^{29}$ to $R^{32}$ are independently selected from hydrogen, halogen, hydrocarbyl, substituted hydrocarbyl, heterohydrocarbyl or substituted heterohydrocarbyl; when any two or more of $R^1$ to $R^4$, $R^1$ and $R^{29}$ to $R^{32}$ are hydrocarbyl, substituted hydrocarbyl, heterohydrocarbyl or substituted heterohydrocarbyl, said two or more can be linked to form one or more cyclic substituents.

Another embodiment of the present invention provides a polymerisation catalyst comprising
(1) a nitrogen-containing transition metal compound of Formula W and
(2) an activating quantity of an activator compound selected from organoaluminium compounds and hydrocarbylboron compounds,

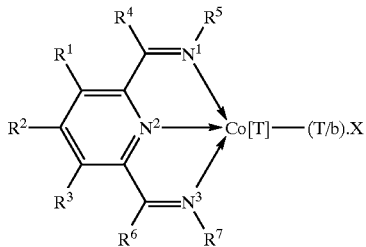

Formula W wherein X represents an atom or group covalently or ionically bonded to the cobalt atom; T is the oxidation state of the cobalt atom and can be Co[I], Co[II], Co[III], and b is the valency of the atom or group X; $R^1$, $R^2$, $R^3$, $R^4$, $R^5$, $R^6$ and $R^7$ are independently selected from hydrogen, halogen, hydrocarbyl, substituted hydrocarbyl, heterohydrocarbyl or substituted heterohydrocarbyl; and when any two or more of $R^1$–$R^7$ are hydrocarbyl, substituted hydrocarbyl, heterohydrocarbyl or substituted heterohydrocarbyl, said two or more can be linked to form one or more cyclic substituents.

In the catalysts of the present invention the transition metal M in the nitrogen-containing complex is preferably Fe(II) or Co(II).

Each of the nitrogen atoms $N^1$, $N^2$ and $N^3$ is coordinated to the transition metal M by a "dative" bond, ie a bond formed by donation of a lone pair of electrons from the nitrogen atom. The remaining bonds on each nitrogen atom are covalent bonds formed by electron sharing between the nitrogen atoms and the organic ligand as shown in the defined formulae for the transition metal complexes illustrated above.

The atom or group represented by X in the compounds of Formulae B, Z, T and W can be, for example, selected from halide, sulphate, nitrate, thiolate, thiocarboxylate, $BF_4^-$; $PF_6^-$; hydride, hydrocarbyloxide, carboxylate, hydrocarbyl, substituted hydrocarbyl and heterohydrocarbyl. Examples of such atoms or groups are chloride, bromide, methyl, ethyl, propyl, butyl, octyl, decyl, phenyl, benzyl, methoxide, ethoxide, isopropoxide, tosylate, triflate, formate, acetate, phenoxide and benzoate. Preferred examples of the atom or group X in the compounds of Formula B, Z, T and W are halide, for example, chloride, bromide; hydride; hydrocarbyloxide, for example, methoxide, ethoxide, isopropoxide, phenoxide; carboxylate, for example, formate, acetate, benzoate; hydrocarbyl, for example, methyl, ethyl, propyl, butyl, octyl, decyl, phenyl, benzyl; substituted hydrocarbyl; heterohydrocarbyl; tosylate; and triflate. Preferably X is selected from halide, hydride and hydrocarbyl. Chloride is particularly preferred.

The following are examples of nitrogen-containing transition metal complexes that can be employed in the catalyst of the present invention:
2,6-diacetylpyridinebis(2,6-diisopropylanil)FeCl$_2$
2,6-diacetylpyridine(2,6-diisopropylanil)MnCl$_2$
2,6-diacetylpyridine(2,6-diisopropylanil)CoCl$_2$
2,6-diacetylpyridinebis(2tert.-butylanil)FeCl$_2$
2,6-diacetylpyridinebis(2,3-dimethylanil)FeCl$_2$
2,6-diacetylpyridinebis(2-methylanil)FeCl$_2$
2,6-diacetylpyridinebis(2,4-dimethylanil)FeCl$_2$
2,6-diacetylpyridinebis(2,6-dimethylanil)FeCl$_2$
2,6-diacetylpyridinebis(2,4,6 trimethylanil)FeCl$_2$
2,6-dialdiminepyridinebis(2,6-dimethylanil)FeCl$_2$
2,6-dialdiminepyridinebis(2,6-diethylanil)FeCl$_2$
2,6-dialdiminepyridinebis(2,6-diisopropylanil)FeCl$_2$
2,6-dialdiminepyridinebis(1-naphthil)FeCl$_2$ and
2,6-bis(1,1-diphenylhydrazone)pyridine.FeCl$_2$.

A preferred complex of the present invention is 2,6-diacetylpyridinebis(2,4,6 trimethylanil)FeCl$_2$.

The activator compound for the catalyst of the present invention is suitably selected from organoaluminium compounds and hydrocarbylboron compounds. Suitable organoaluminium compounds include trialkyaluminium compounds, for example, trimethylaluminium, triethylaluminium, tributylaluminium, tri-n-octylaluminium, ethylaluminium dichloride, diethylaluminium chloride and alumoxanes. Alumoxanes are well known in the art as typically the oligomeric compounds which can be prepared by the controlled addition of water to an alkylaluminium compound, for example trimethylatuminium. Such compounds can be linear, cyclic or mixtures thereof. Commercially available alumoxanes are generally believed to be mixtures of linear and cyclic compounds. The cyclic alumoxanes can be represented by the formula [$R^{16}$AlO], and the linear alumoxanes by the formula $R^{17}$($R^{18}$AlO), wherein s is a number from about 2 to 50, and wherein $R^{16}$, $R^{17}$, and $R^{18}$ represent hydrocarbyl groups, preferably $C_1$ to $C_6$ all groups, for example methyl, ethyl or butyl groups.

Examples of suitable hydrocarbylboron compounds are dimethylphenylammoniumtetra(phenyl)borate, trityltetra(phenyl)borate, triphenylboron, dimethylphenylammonium tetra(pentafluorophenyl)borate, sodium tetrakis[(bis-3,5-trifluoromethyl)phenyl]borate, $H^+(OEt_2)$[(bis-3,5-trifluoromethyl)phenyl]borate, trityltetra(pentafluorophenyl)borate and tris(pentafluorophenyl)boron.

In the preparation of the catalysts of the present invention the quantity of activating compound selected from organoaluminium compounds and hydrocarbylboron compounds to be employed is easily determined by simple testing, for example, by the preparation of small test samples which can be used to polymerise small quantities of the monomer(s) and thus to determine the activity of the produced catalyst. It is generally found that the quantity employed is sufficient to provide 0.1 to 20,000 atoms, preferably 1 to 2000 atoms of aluminium or boron per Fe, Co, Mn or Ru metal atom in the compound of Formula B, Z, T or W.

In the compound of Formula B of the present invention, M is preferably Fe[II]. In the compounds of Formula Z or Formula T of the present invention, M is preferably Fe[II], Mn[II] or Co[II].

A further aspect of the present invention provides a polymerisation catalyst system comprising (1) as the transition metal compound, a compound having the Formula B, Z, T or W (2) an activating quantity of an activator compound selected from organoaluminium and hydrocarbylboroncompounds and (3) a neutral Lewis base.

In this further aspect of the present invention, the iron and cobalt compounds are preferred. The preferences in relation to the activator compound are the same as expressed above in relation to the catalysts of the present invention. Neutral Lewis bases are well known in the art of Ziegler-Natta catalyst polymerisation technology. Examples of classes of neutral Lewis bases suitably employed in the present invention are unsaturated hydrocarbons, for example, alkenes (other than 1-olefins) or alkynes, primary, secondary and tertiary amines, amides, phosphoramides, phosphines, phosphites, ethers, thioethers, nitriles, carbonyl compounds, for example, esters, ketones, aldehydes, carbon monoxide and carbon dioxide, sulphoxides, sulphones and boroxines. Although 1-olefins are capable of acting as neutral Lewis bases, for the purposes of the present invention they are regarded as monomer or comonomer 1-olefins and not as neutral Lewis bases per se. However, alkenes which are internal olefins, for example, 2-butene and cyclohexene are regarded as neutral Lewis bases in the present invention. Preferred Lewis bases are tertiary amines and aromatic esters, for example, dimethylaniline, diethylaniline, tributylamine, ethylbenzoate and benzylbenzoate. In this particular aspect of the present invention, components (1), (2) and (3) of the catalyst system can be brought together simultaneously or in any desired order. However, if components (2) and (3) are compounds which interact together strongly, for example, form a stable compound together, it is preferred to bring together either components (1) and (2) or components (1) and (3) in an initial step before introducing the final defined component. Preferably components (1) and (3) are contacted together before component (2) is introduced. The quantities of components (1) and (2) employed in the preparation of this catalyst system are suitably as described above in relation to the catalysts of the present invention. The quantity of the neutral Lewis Base [component (3)] is preferably such as to provide a ratio of component (1):component (3) in the range 100:1 to 1:1000, most preferably in the range 1:1 to 1:20. Components (1), (2) and (3) of the catalyst system can brought together, for example, as the neat materials, as a suspension or solution of the materials in a suitable diluent or solvent (for example a liquid hydrocarbon), or, if at least one of the components is volatile, by utilising the vapour of that component. The components can be brought together at any desired temperature. Mixing the components together at room temperature is generally satisfactory. Heating to higher temperatures eg up to 120° C. can be carried out if desired, eg to achieve better mixing of the components. It is preferred to carry out the bringing together of components (1), (2) and (3) in an inert atmosphere (eg dry nitrogen) or in vacuo. If it is desired to use the catalyst on a support material (see below), this can be achieved, for example, by performing the catalyst system comprising components (1), (2) and (3) and impregnating the support material preferably with a solution thereof or by introducing to the support material one or more of the components simultaneously or sequentially. If desired the support material itself can have the properties of a neutral Lewis base and can be employed as, or in place of, component (3). An example of a support material having neutral Lewis base properties is poly(aminostyrene) or a copolymer of styrene and aminostyrene (ie vinylaniline).

The catalysts of the present invention can if desired comprise more than one of the defined transition metal compounds. The catalyst may comprise, for example a mixture of 2,6-diacetylpyridinebis(2,6-diisopropylanil) $FeCl_2$ complex and 2,6-diacetylpyridinebis(2,4,6-trimethylanil)$FeCl_2$ complex, or a mixture of 2,6-diacetylpyridine(2,6-diisopropylanil)$CoCl_2$ and 2,6-diacetylpyridinebis(2,4,6-trimethylanil)$FeCl_2$. In addition to said one or more defined transition metal compounds, the catalysts of the present invention can also include one or more other types of transition metal compounds or catalysts, for example, transition metal compounds of the type used in conventional Ziegler-Natta catalyst systems, metallocene-based catalysts, or heat activated supported chromium oxide catalysts (eg Phillips-type catalyst).

The catalysts of the present invention can be unsupported or supported on a support material, for example, silica, alumina, or zirconia, or on a polymer or prepolymer, for example polyethylene, polystyrene, or poly(aminostyrene).

Thus a preferred embodiment of the present invention provides a catalyst comprising (1) a nitrogen-containing transition metal compound having the following Formula B, and (2) an activating quantity of an activator compound selected from organoaluminium compounds and hydrocarbylboron compounds, Formula B

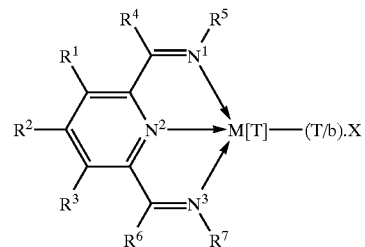

wherein M is Fe[II], Fe[III], Co[I], Co[II], Co[III], Ru[II], Ru[III], Ru[IV], Mn[I], Mn[II], Mn[III] or Mn[MV]; X represents an atom or group covalently or ionically bonded to the transition metal M; T is the oxidation state of the transition metal M and b is the valency of the atom or group X; $R^1$, $R^2$, $R^3$, $R^4$, and $R^6$ are independently selected from hydrogen, halogen, hydrocarbyl, substituted hydrocarbyl, heterohydrocarbyl or substituted heterohydrocarbyl;

and such that (1):

when M is Fe, Co or Ru, $R^5$ and $R^7$ are independently selected from hydrogen, halogen, hydrocarbyl, substituted hydrocarbyl, heterohydrocarbyl or substituted heterohydrocarbyl; and when any two or more of $R^1$–$R^7$ are hydrocarbyl, substituted hydrocarbyl, heterohydrocarbyl or substituted heterohydrocarbyl, said two or more can be linked to form one or more cyclic substituents, or such that (2):

when M is Fe, Co, Mn or Ru, then Rs is represented by the group "P" and $R^7$ is represented by the group "Q" as follows:

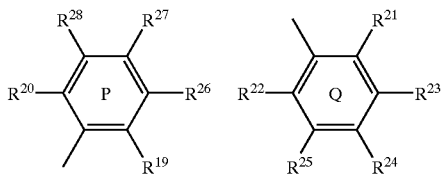

wherein $R^{19}$ to $R^{28}$ are independently selected from hydrogen, halogen, hydrocarbyl, substituted hydrocarbyl, heterohydrocarbyl or substituted heterohydrocarbyl; when any two or more of $R^1$ to $R^4$, $R^6$ and $RW^{19}$ to $R^{28}$ are hydrocarbyl, substituted hydrocarbyl, heterohydrocarbyl or substituted heterohydrocarbyl, said two or more can be linked to form one or more cyclic substituents; with the proviso that at least one of $R^{19}$, $R^{20}$, $R^{21}$ and $R^{22}$ is hydrocarbyl, substituted hydrocarbyl, heterohydrocarbyl or substituted heterohydrocarbyl when neither of the ring systems P and Q forms part of a polyaromatic fused-ring system, or such that (3)

when M is Fe, Co, Mn or Ru, then $R^5$ is a group having the formula —$NR^{29}R^{30}$ and $R^7$ is a group having the formula —$NR^{31}R^{32}$, wherein $R^{29}$ to $R^{32}$ are independently selected from hydrogen, halogen, hydrocarbyl, substituted hydrocarbyl, heterohydrocarbyl or substituted heterohydrocarbyl; when any two or more of $R^1$ to $R^4$, $R^6$ and $R^{29}$ to $R^{32}$ are hydrocarbyl, substituted hydrocarbyl, heterohydrocarbyl or substituted heterohydrocarbyl, said two or more can be linked to form one or more cyclic substituents, characterised in that the catalyst is supported on a support material.

If desired the catalysts can be formed in situ in the presence of the support material, or the support material can be pre-impregnated or premixed, simultaneously or sequentially, with one or more of the catalyst components. The catalysts of the present invention can if desired be supported on a heterogeneous catalyst, for example, a magnesium halide supported Ziegler Natta catalyst, a Phillips type (chromium oxide) supported catalyst or a supported metallocene catalyst. Formation of the supported catalyst can be achieved for example by treating the transition metal compounds of the present invention with alumoxane in a suitable inert diluent, for example a volatile hydrocarbon, slurrying a particulate support material with the product and evaporating the volatile diluent. The produced supported catalyst is preferably in the form of a free-flowing powder. The quantity of support material employed can vary widely, for example from 100,000 to 1 grams per gram of metal present in the transition metal compound.

The present invention further provides a process for the polymerisation and copolymerisation of 1-olefins comprising contacting the monomeric olefin under polymerisation conditions with the polymerisation catalyst of the present invention.

In the polymerisation process of the present invention the polymerisation catalyst is preferably based on the Formula B, T, W or Z compounds as described above.

The polymerisation conditions can be, for example, solution phase, slurry phase or gas phase. If desired, the catalyst can be used to polymerise ethylene under high pressure/high temperature process conditions wherein the polymeric material forms as a melt in supercritical ethylene. Preferably the polymerisation is conducted under gas phase fluidised bed conditions.

Slurry phase polymerisation conditions or gas phase polymerisation conditions are particularly useful for the production of high density grades of polyethylene. In these processes the polymerisation conditions can be batch, continuous or semi-continuous. In the slurry phase process and the gas phase process, the catalyst is generally fed to the polymerisation zone in the form of a particulate solid. This solid can be, for example, an undiluted solid catalyst system formed from a nitrogen-containing complex and an activator, or can be the solid complex alone. In the latter situation, the activator can be fed to the polymerisation zone, for example as a solution, separately from or together with the solid complex. Preferably the catalyst system or the transition metal complex component of the catalyst system employed in the slurry polymerisation and gas phase polymeriastion is supported on a support material. Most preferably the catalyst system is supported on a support material prior to its introduction into the polymerisation zone. Suitable support materials are, for example, silica, alumina, zirconia, talc, kieselguhr, or magnesia. Impregnation of the support material can be carried out by conventional techniques, for example, by forming a solution or suspension of the catalyst components in a suitable diluent or solvent, and slurrying the support material therewith. The support material thus impregnated with catalyst can then be separated from the diluent for example, by filtration or evaporation techniques.

In the slurry phase polymerisation process the solid particles of catalyst, or supported catalyst, are fed to a polymerisation zone either as dry powder or as a slurry in the polymerisation diluent. Preferably the particles are fed to a polymerisation zone as a suspension in the polymerisation diluent. The polymerisation zone can be, for example, an autoclave or similar reaction vessel, or a continuous loop reactor, eg of the type well-know in the manufacture of polyethylene by the Phillips Process. When the polymerisation process of the present invention is carried out under slurry conditions the polymerisation is preferably carried out at a temperature above 0° C., most preferably above 15° C. The polymerisation temperature is preferably maintained below the temperature at which the polymer commences to soften or sinter in the presence of the polymerisation diluent. If the temperature is allowed to go above the latter temperature, fouling of the reactor can occur. Adjustment of the polymerisation within these defined temperature ranges can provide a useful means of controlling the average molecular weight of the produced polymer. A further useful means of controlling the molecular weight is to conduct the polymerisation in the presence of hydrogen gas which acts as chain transfer agent. Generally, the higher the concentration of hydrogen employed, the lower the average molecular weight of the produced polymer.

The use of hydrogen gas as a means of controlling the average molecular weight of the polymer or copolymer applies generally to the polymerisation process of the present invention. For example, hydrogen can be used to reduce the average molecular weight of polymers or copolymers prepared using gas phase, slurry phase or solution phase polymerisation conditions. The quantity of hydrogen gas to be employed to give the desired average molecular weight can be determined by simple "trial and error" polymerisation tests.

The polymerisation process of the present invention provides polymers and copolymers, especially ethylene polymers, at remarkably high productivity (based on the amount of polymer or copolymer produced per unit weight of nitrogen-containing transition metal complex employed in the catalyst system). This means that relatively very small quantities of transition metal complex are consumed in commercial processes using the process of the present invention. It also means that when the polymerisation process of the present invention is operated under polymer recovery conditions that do not employ a catalyst separation step, thus leaving the catalyst, or residues thereof, in the polymer (eg as occurs in most commercial slurry and gas phase polymerisation processes), the amount of transition metal complex in the produced polymer can be very small. Experiments carried out with the catalyst of the present invention show that, for example, polymerisation of ethylene under slurry polymerisation conditions can provide a particulate polyethylene product containing catalyst so diluted by the produced polyethylene that the concentration of transition metal therein falls to, for example, 1 ppm or less wherein "ppm" is defined as parts by weight of transition metal per million parts by weight of polymer. Thus polyethylene produced within a polymerisation reactor by the process of the present invention may contain catalyst diluted with the polyethylene to such an extent that the transition metal content thereof is, for example, in the range of 1–0.0001 ppm, preferably 1–0.001 ppm. Using a catalyst comprising a nitrogen-containing Fe complex in accordance with the present invention in, for example, a slurry polymerisation, it is possible to obtain polyethylene powder wherein the Fe concentration is, for example, 1.03 to 0.11 parts by weight of Fe per million parts by weight of polyethylene.

Suitable monomers for use in the polymerisation process of the present invention are, for example, ethylene, propylene, butene, hexene, methyl methacrylate, methyl acrylate, butyl acrylate, acrylonitrile, vinyl acetate, and styrene. Preferred monomers for homopolymerisation processes are ethylene and propylene. The catalyst can also be used for copolymerising ethylene with other 1-olefins such as propylene, 1-butene, 1-hexene, 4-methylpentene-1, and octene.

Thus the present invention further provides a process comprising contacting ethylene and one or more other 1-olefins with a catalyst comprising (1) a nitrogen-containing transition metal compound having the following Formula B, and
(2) an activating quantity of an activator compound selected from organoaluminium compounds and hydrocarbylboron compounds,

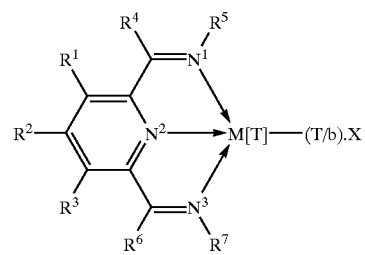

Formula B wherein M is Fe[II], Fe[III], Co[I], Co[II], Co[III], Ru[II], Ru[III], Ru[IV], Mn[I], Mn[II], Mn[III] or Mn[IV]; X represents an atom or group covalently or ionically bonded to the transition metal M; T is the oxidation state of the transition metal M and b is the valency of the atom or group X; $R^1$, $R^2$, $R^3$, $R^4$, and $R^6$ are independently selected from hydrogen, halogen, hydrocarbyl, substituted hydrocarbyl, heterohydrocarbyl or substituted heterohydrocarbyl;

and such that (1):
when M is Fe, Co or Ru, $R^5$ and $R^7$ are independently selected from hydrogen, halogen, hydrocarbyl, substituted hydrocarbyl, heterohydrocarbyl or substituted heterohydrocarbyl; and when any two or more of $R^1$–$R^7$ are hydrocarbyl, substituted hydrocarbyl, heterohydrocarbyl or substituted heterohydrocarbyl, said two or more can be linked to form one or more cyclic substituents, or such that (2):
when M is Fe, Co, Mn or Ru, then $R^5$ is represented by the group "P" and $R^7$ is represented by the group "Q" as follows:

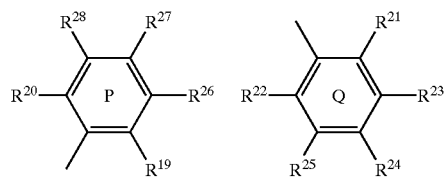

wherein $R^{19}$ to $R^{28}$ are independently selected from hydrogen, halogen, hydrocarbyl, substituted hydrocarbyl, heterohydrocarbyl or substituted heterohydrocarbyl; when any two or more of $R^1$ to $R^4$, $R^6$ and $R^{19}$ to $R^{28}$ are hydrocarbyl, substituted hydrocarbyl, heterohydrocarbyl or substituted heterohydrocarbyl, said two or more can be linked to form one or more cyclic substituents; with the proviso that at least one of $R^{19}$, $R^{20}$, $R^{21}$ and $R^{22}$ is hydrocarbyl, substituted hydrocarbyl, heterohydrocarbyl or substituted heterohydrocarbyl when neither of the ring systems P and Q forms part of a polyaromatic fused-ring system, or such that (3)
when M is Fe, Co, Mn or Ru, then $R^5$ is a group having the formula —$NR^{29}R^{30}$ and $R^7$ is a group having the formula —$NR^{31}R^{32}$, wherein $R^{29}$ to $R^{32}$ are independently selected from hydrogen, halogen, hydrocarbyl, substituted hydrocarbyl, heterohydrocarbyl or substituted heterohydrocarbyl; when any two or more of $R^1$ to $R^4$, $R^6$ and $R^{29}$ to $R^{32}$ are hydrocarbyl, substituted hydrocarbyl, heterohydrocarbyl or substituted heterohydrocarbyl, said two or more can be linked to form one or more cyclic substituents.

The catalyst of the present invention can also be used for copolymerising ethylene with other monomeric materials, for example, methyl methacrylate, methyl acrylate, butyl acrylate, acrylonitrile, vinyl acetate, and styrene.

A preferred embodiment of the present invention comprises a process for the polymerisation and copolymerisation of 1-olefins comprising contacting the monomeric olefin under polymerisation conditions with a polymerisation catalyst comprising (1) a nitrogen-containing transition metal compound having the following Formula B, and (2) an activating quantity of an activator compound selected from organoaluminium compounds and hydrocarbylboron compounds,

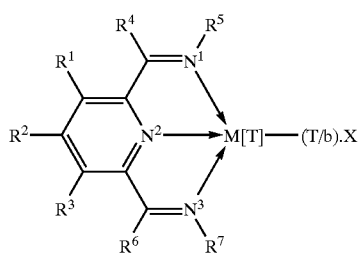

Formula B wherein M is Fe[II], Fe[III], Co[I], Co[II], Co[III], Ru[II], Ru[III], Ru[IV], Mn[I], Mn[II], Mn[III] or Mn[IV]; X represents an atom or group covatently or ionically bonded to the transition metal M; T is the oxidation state of the transition metal M and b is the valency of the atom or group X; $R^1$, $R^2$, $R^3$, $R^4$, and $R^6$ are independently selected from hydrogen, halogen, hydrocarbyl, substituted hydrocarbyl, heterohydrocarbyl or substituted heterohydrocarbyl;

and such that (1):

when M is Fe, Co or Ru, $R^5$ and $R^7$ are independently selected from hydrogen, halogen, hydrocarbyl, substituted hydrocarbyl, heterohydrocarbyl or substituted heterohydrocarbyl; and when any two or more of $R^1$–$R^7$ are hydrocarbyl, substituted hydrocarbyl, heterohydrocarbyl or substituted heterohydrocarbyl, said two or more can be linked to form one or more cyclic substituents, or such that (2):

when M is Fe, Co, Mn or Ru, then $R^1$ is represented by the group "P" and $R^7$ is represented by the group "Q" as follows:

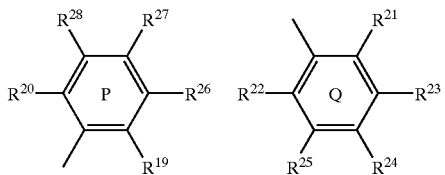

wherein $R^{19}$ to $R^{28}$ are independently selected from hydrogen, halogen, hydrocarbyl, substituted hydrocarbyl, heterohydrocarbyl or substituted heterohydrocarbyl; when any two or more of $R^1$ to $R^4$, $R^6$ and $R^{19}$ to $R^{28}$ are hydrocarbyl, substituted hydrocarbyl, heterohydrocarbyl or substituted heterohydrocarbyl, said two or more can be linked to form one or more cyclic substituents; with the proviso that at least one of $R^{19}$, $R^{20}$, $R^{21}$ and $R^{22}$ is hydrocarbyl, substituted hydrocarbyl, heterohydrocarbyl or substituted heterohydrocarbyl when neither of the ring systems P and Q forms part of a polyaromatic fiused-ring system, or such that (3)

when M is Fe, Co, Mn or Ru, then $R^5$ is a group having the formula —$NR^{29}R^{30}$ and $R^7$ is a group having the formula —$NR^{31}R^{32}$, wherein $R^{29}$ to $R^{32}$ are independently selected from hydrogen, halogen, hydrocarbyl, substituted hydrocarbyl, heterohydrocarbyl or substituted heterohydrocarbyl; when any two or more of $R^1$ to $R^4$, $R^6$ and $R^{29}$ to $R^{32}$ are hydrocarbyl, substituted hydrocarbyl, heterohydrocarbyl or substituted heterohydrocarbyl, said two or more can be linked to form one or more cyclic substituents characterised in that the polymerisation conditions are gas phase polymerisation conditions.

Methods for operating gas phase polymerisation processes are well known in the art. Such methods generally involve agitating (eg by stirring, vibrating or fluidising) a bed of catalyst, or a bed of the target polymer (ie polymer having the same or similar physical properties to that which it is desired to make in the polymerisation process) containing a catalyst, and feeding thereto a stream of monomer at least partially in the gaseous phase, under conditions such that at least part of the monomer polymerises in contact with the catalyst in the bed. The bed is generally cooled by the addition of cool gas (eg recycled gaseous monomer) and/or volatile liquid (eg a volatile inert hydrocarbon, or gaseous monomer which has been condensed to form a liquid). The polymer produced in, and isolated from, gas phase processes forms directly a solid in the polymerisation zone and is free from, or substantially free from liquid. As is well known to those skilled in the art, if any liquid is allowed to enter the polymerisation zone of a gas phase polymerisation process the quantity of liquid is small in relation to the quantity of polymer present in the polymerisation zone. This is in contrast to "solution phase" processes wherein the polymer is formed dissolved in a solvent, and "slurry phase" processes wherein the polymer forms as a suspension in a liquid diluent.

The gas phase process can be operated under batch, semi-batch, or so-called "continuous" conditions. It is preferred to operate under conditions such that monomer is continuously recycled to an agitated polymerisation zone containing polymerisation catalyst, make-up monomer being provided to replace polymerised monomer, and continuously or intermittently withdrawing produced polymer from the polymerisation zone at a rate comparable to the rate of formation of the polymer, fresh catalyst being added to the polymerisation zone to replace the catalyst withdrawn form the polymerisation zone with the produced polymer.

In the preferred embodiment of the gas phase polymerisation process of the present invention, the gas phase polymerisation conditions are preferably gas phase fluidised bed polymerisation conditions.

Methods for operating gas phase fluidised bed processes for making polyethylene and ethylene copolymers are well known in the art. The process can be operated, for example, in a vertical cylindrical reactor equipped with a perforated distribution plate to support the bed and to distribute the incoming fluidising gas stream through the bed. The fluidising gas circulating through the bed serves to remove the heat of polymerisation from the bed and to supply monomer for polymerisation in the bed. Thus the fluidising gas generally comprises the monomer(s) normally together with some inert gas (eg nitrogen) and optionally with hydrogen as molecular weight modifier. The hot fluidising gas emerging from the top of the bed is led optionally through a velocity reduction zone (this can be a cylindrical portion of the reactor having a wider diameter) and, if desired, a cyclone and or filters to disentrain fine solid particles from the gas stream. The hot gas is then led to a heat exchanger to remove at least part of the heat of polymerisation. Catalyst is preferably fed continuously or at regular intervals to the bed. At start up of the process, the bed comprises fluidisable polymer which is preferably similar to the target polymer. Polymer is produced continuously within the bed by the polymerisation of the monomer(s). Preferably means are provided to discharge polymer from the bed continuously or at regular intervals to maintain the fluidised bed at the desired height. The process is generally operated at relatively low pressure, for example, at 10 to 50 bars, and at temperatures for example, between 50 and 120° C. The temperature of the bed is maintained below the sintering temperature of the fluidised polymer to avoid problems of agglomeration.

In the gas phase fluidised bed process for polymerisation of olefins the heat evolved by the exothermic polymerisation reaction is normally removed from the polymerisation zone (ie, the fluidised bed) by means of the fluidising gas stream as described above. The hot reactor gas emerging from the top of the bed is led through one or more heat exchangers wherein the gas is cooled. The cooled reactor gas, together with any make-up gas, is then recycled to the base of the bed. In the gas phase fluidised bed polymerisation process of the present invention it is desirable to provide additional cooling of the bed (and thereby improve the space time yield of the process) by feeding a volatile liquid to the bed under conditions such that the liquid evaporates in the bed thereby absorbing additional heat of polymerisation from the bed by the "latent heat of evaporation" effect. When the hot recycle gas from the bed enters the heat exchanger, the volatile liquid can condense out. In one embodiment of the present invention the volatile liquid is separated from the recycle gas and reintroduced separately into the bed. Thus, for example, the volatile liquid can be separated and sprayed into the bed. In another embodiment of the present invention the volatile liquid is recycled to the bed with the recycle gas. Thus the volatile liquid can be condensed from the fluidising gas stream emerging from the reactor and can be recycled to the bed with recycle gas, or can be separated from the recycle gas and sprayed back into the bed.

The method of condensing liquid in the recycle gas stream and returning the mixture of gas and entrained liquid to the bed is described in EP-A-008969 1 and EP-A-0241947. It is preferred to reintroduce the condensed liquid into the bed separate from the recycle gas using the process described in our U.S. Pat. No. 5,541,270, the teaching of which is hereby incorporated into this specification,.

When using the catalysts of the present invention under gas phase polymerisation conditions, the catalyst, or one or more of the components employed to form the catalyst can, for example, be introduced into the polymerisation reaction zone in liquid form, for example, as a solution in an inert liquid diluent. Thus, for example, the transition metal component, or the activator component, or both of these components can be dissolved or slurried in a liquid diluent and fed to the polymerisation zone. Under these circumstances it is preferred the liquid containing the component(s) is sprayed as fine droplets into the polymerisation zone. The droplet diameter is preferably within the range 1 to 1000 microns. EP-A-0593083, the teaching of which is hereby incorporated into this specification, discloses a process for introducing a polymerisation catalyst into a gas phase polymerisation. The methods disclosed in EP-A-0593083 can be suitably employed in the polymerisation process of the present invention if desired.

The present invention further provides a novel nitrogen-containing transition metal compound comprising the skeletal unit depicted in Formula Z:

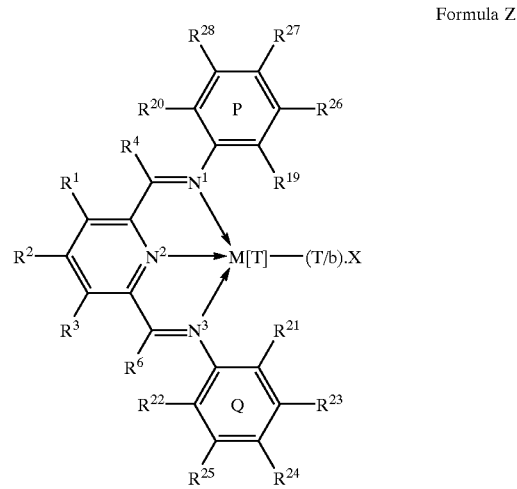

Formula Z wherein M is Fe[II], Fe[III], Co[I], Co[II], Co[III], Mn[I], Mn[II], Mn[III], Mn[IV], Ru[II], Ru[III] or Ru[IV]; X represents an atom or group covalently or ionically bonded to the transition metal M; T is the oxidation state of the transition metal M and b is the valency of the atom or group X; $R^1$ to $R^4$, $R^6$ and $R^{19}$ to $R^{28}$ are independently selected from hydrogen, halogen, hydrocarbyl, substituted hydrocarbyl, heterohydrocarbyl or substituted heterohydrocarbyl; when any two or more of $R^1$ to $R^4$, $R^6$ and $R^{19}$ to $R^{28}$ are hydrocarbyl, substituted hydrocarbyl, heterohydrocarbyl or substituted heterohydrocarbyl, said two or more can be linked to form one or more cyclic substituents; with the proviso that at least one of $R^{19}$, $R^{20}$, $R^{21}$ and $R^{22}$ is hydrocarbyl, substituted hydrocarbyl, heterohydrocarbyl or substituted heterohydrocarbyl when neither of the ring systems P and Q forms part of a polyaromatic fused-ring system. In this particular aspect of the present invention, in the case that neither of the ring systems P and Q forms part of a polyaromatic ring system, it is preferred that at least one of $R^{19}$ and $R^{20}$, and at least one of $R^{21}$ and $R^{22}$ is selected from hydrocarbyl, substituted hydrocarbyl, heterohydrocarbyl or substituted heterohydrocarbyl. In one embodiment of the present invention, $R^{19}$, $R^{20}$, $R^{21}$ and $R^{22}$ are hydrocarbyl, substituted hydrocarbyl, heterohydrocarbyl or substituted heterohydrocarbyl when neither of the ring systems P and Q forms part of a polyaromatic fused-ring system.

Subject to the foregoing provisos regarding $R^{19}$, $R^{20}$, $R^{21}$ and $R^{22}$ in Formula Z, $R^1$ to $R^4$, $R^6$ and $R^{19}$ to $R^{28}$ in the compounds depicted in Formulae B and Z of the present invention are preferably independently selected from hydrogen and $C_1$ to $C_8$ hydrocarbyl, for example, methyl, ethyl, n-propyl, n-butyl, n-hexyl, and n-octyl. In Formula B, $R^5$ and $R^7$ are preferably independently selected from substituted or unsubstituted alicyclic, heterocyclic or aromatic groups, for example, phenyl, 1-naphthyl, 2-naphthyl, 2-methylphenyl, 2-ethylphenyl, 2,6-diisopropylphenyl, 2,3-diisopropylphenyl, 2,4-diisopropylphenyl, 2,6-di-n-butylphenyl, 2,6-dimethylphenyl, 2,3-dimethylphenyl, 2,4-dimethylphenyl, 2-t-butylphenyl, 2,6-diphenylphenyl, 2,4,6-trimethylphenyl, 2,6-trifluoromethylphenyl, 4-bromo-2,6-dimethylphenyl, 3,5 dichloro2,6-diethylphenyl, and 2,6,bis (2,6-dimethylphenyl)phenyl, cyclohexyl and pyridinyl.

The ring systems P and Q in Formula Z are preferably independently 2,6-hydrocarbylphenyl or fused-ring polyaromatic, for example, 1-naphthyl, 2-naphthyl, 1-phenanthrenyl and 8-quinolinyl.

Yet another aspect of the present invention provides a novel nitrogen-containing transition metal compound comprising the skeletal unit depicted in Formula T:

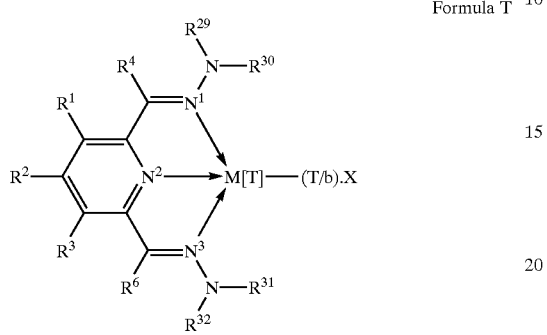

Formula T wherein M is Fe[II], Fe[III], Co[I], Co[II], Co[III], Mn[I], Mn[II], Mn[III], Mn[IV], Ru[II], Ru[III] or Ru[IV]; X represents an atom or group covalently or ionically bonded to the transition metal M; T is the oxidation state of the transition metal M and b is the valency of the atom or group X; $R^1$ to $R^4$, $R^6$ and $R^{29}$ to $R^{32}$ are independently selected from hydrogen, halogen, hydrocarbyl, substituted hydrocarbyl, heterohydrocarbyl or substituted heterohydrocarbyl; when any two or more of $R^1$ to $R^4$, $R^6$ and $R^{29}$ to $R^{32}$ are hydrocarbyl, substituted hydrocarbyl, heterohydrocarbyl or substituted heterohydrocarbyl, said two or more can be linked to form one or more cyclic substituents.

A further aspect of the invention comprises the use of the compounds defined previously as catalysts for the polymerisation or co-polymerisation of 1-olefins.

The following are examples of novel nitrogen-containing transition metal complexes of the present invention:

2,6-diacetylpyridinebis(2,6-diisopropylanil)FeCl$_2$
2,6-diacetylpyridine(2,6-diisopropylanil)MnCl$_2$
2,6-diacetylpyridine(2,6-diisopropylanil)CoCl$_2$
2,6-diacetylpyridinebis(2-tert.-butylanil)FeCl$_2$
2,6-diacetylpyridinebis(2,3-dimethylanil)FeCl$_2$
2,6-diacetylpyridinebis(2-methylanil)FeCl$_2$
2,6-diacetylpyridinebis(2,4-dimethylanil)FeCl$_2$
2,6-diacetylpyridinebis(2,6-dimethylanil)FeCl$_2$
2,6-diacetylpyridinebis(2,4,6-trimethylanil)FeCl$_2$
2,6-dialdiminepyridinebis(2,6-dimethylanil)FeCl$_2$
2,6-dialdiminepyridinebis(2,6-diethylanil)FeCl$_2$
2,6-dialdiminepyridinebis(2,6-diisopropylanil)FeCl$_2$
2,6-dialdiminepyridinebis(1-naphthil)FeCl$_2$ and
2,6-bis(1,1-diphenylhydrazone)pyridine.FeCl$_2$.
2,6-diacetylpyridinebis(2,4,6-trimethylanil)FeCl$_2$ is preferred.

The present invention further provides novel compounds useful for making polymerisation catalysts comprising a compound having the general Formula E as follows:

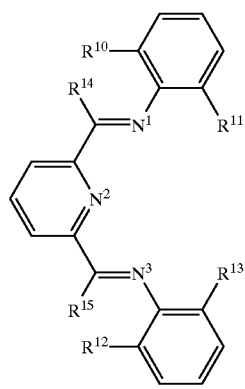

Formula E wherein $R^{10}$, $R^{11}$, $R^{12}$ and $R^{13}$ are independently selected from $C_1$ to $C_{20}$ hydrocarbon groups; and $R^{14}$, $R^{15}$ and all the remaining ring substituents on the pyridine and benzene rings depicted in Formula E are independently selected from hydrogen and $C_1$ to $C_{20}$ hydrocarbon groups.

The production of ligands for preparing the nitrogen containing transition metal complexes used in the present invention is conventional synthetic organic chemistry. For example, ligands of the type shown attached to the transition metal atom in Formula B can be made, for example, by reacting together a substituted or unsubstituted 2,6-dicarboxaldehydepyridine or 2,6-diacylpyridine compound (ie having the appropriate $R^1$, $R^2$, $R^3$, $R^4$ and $R^6$ substituents) with two molar equivalents of a diamine bearing the desired substituents $R^5$ and $R^7$.

The present invention further provides novel compounds useful for making polymerisation catalysts comprising a compound having the general Formula P as follows:

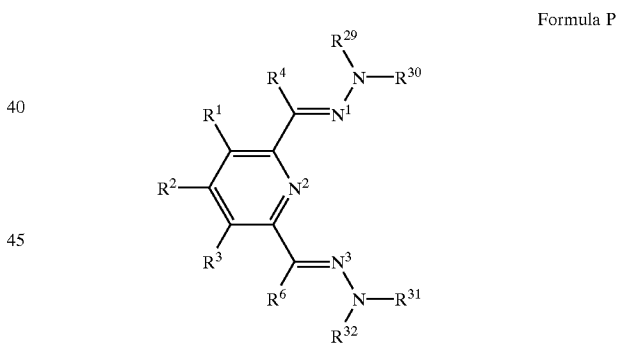

Formula P wherein $R^1$ to $R^4$, $R^6$ and $R^{29}$ to $R^{32}$ are independently selected from hydrogen, halogen, hydrocarbyl, substituted hydrocarbyl, heterohydrocarbyl or substituted heterohydrocarbyl; when any two or more of $R^1$ to $R^4$, $R^6$ and $R^{29}$ to $R^{32}$ are hydrocarbyl, substituted hydrocarbyl, heterohydrocarbyl or substituted heterohydrocarbyl, said two or more can be linked to form one or more cyclic substituents. Preferably $R^{29}$, $R^{30}$, $R^{31}$, and $R^{32}$ are hydrocarbyl. Most preferably at least one of $R^{29}$ and $R^{30}$, and at least one of $R^{31}$ and $R^{32}$ are aryl groups, for example, phenyl, naphthyl, or substituted phenyl. Ligands of the type shown in Formula P can be prepared by well-known methods, for example by reaction of a substituted or unsubstituted 2,6-di(carboxaldehyde) pyridine or 2,6-diacylpyridine compound (ie having the appropriate $R^1$, $R^2$, $R^3$, $R^4$ and $R^6$ substituents) with two molar equivalents of a hydrazine compound bearing the desired substituents $R^{29}$, $R^{30}$, $R^{31}$ and $R^{32}$.

Thus ligands of the type illustrated, for example, in Formulae B, Z, T, E and P can generally be prepared by condensation reactions between bis(carbonyl)pyridine compounds and appropriate amines or hydrazines. Such reactions can be catalysed, for example, by acids, for example, acetic acid or toluene-p-sulphonic acid. During reactions of this type it is normally advantageous to remove from the reaction zone the water eliminated by the reaction of the carbonyl groups with the —NH$_2$ groups In the preparation of ligands using this type of reaction, it is preferred to take off the water by refluxing the reaction mixture with an azeotrope-forming water-immiscible liquid, and separating and removing the water from the distillate in a suitable reflux head, eg in a Dean and Stark head. Suitable liquids for this purpose are, for example, hydrocarbons, especially aromatic hydrocarbons such as toluene or xylene.

The present invention is illustrated in the following Examples.

EXAMPLES

Example 1 shows the preparation of an iron compound (see Formula D below), Example 2 shows the preparation of a manganese compound (see Formula J below) and Example 3 shows the preparation of a cobalt compound (see Formula K), for preparing the catalyst of the present invention. Runs 1.1 to 1.6, 2.1, 3.1 and 3.2 illustrate the use of these compounds as catalysts in the polymerisation of ethylene in accordance with the catalyst and process of the present invention.

In the Examples all manipulations of air/moisture-sensitive materials were performed on a conventional vacuumninert atmosphere (nitrogen) line using standard Schlenk line techniques, or in an inert atmosphere glove box.

Example 1

Intermediate A [2,6-diacetylpyridinebis(2,6-diisopropylanil)] was prepared by the reaction of Intermediate B [2,6-diacetylpyridine] and Intermediate C [2,6-diisopropylaniline]. Intermediate A was then reacted with ferrous chloride in butanol to provide the compound of Formula D.

Preparation of Intermediate A

Using a procedure based on a related preparation (E. C. Alyea and P. H. Merrell, Synth. React. Inorg. Metal-Org. Chem., 1974, 4, 535):—2,6-diisopropylaniline (3.46 ml, 18.4 mmol) was added dropwise to a solution of 2,6-diacetylpyridine (1.50 g, 9.2 mmol) in absolute ethanol (25 ml) [2,6-diisopropylaniline and 2,6-diacetylpyridine were obtained from Aldrich the former of which was freshly distilled before use]. A few drops of glacial acetic acid was added and the solution was refluxed for 48 h. Concentration of the solution to half volume and cooling to −78° C. gave intermediate A as pale yellow crystals (80%). Calcd for $C_{33}H_{43}N_3$: C, 82.3; H. 8.9; N, 8.7; Found: C, 81.9; H, 8.5; 8.7%. FABMS: M+ (481). $^1$H NMR (CDCl$_3$): 8.6–7.9[m, 3H, C$_5$H$_3$N], 7.2–6.9[m, 6H, C$_6$(CHMe$_2$)H$_3$], 2.73[sept, 4H, CHMe$_2$], 2.26[s, 6H, C$_5$H$_3$N(CMeNAr)$_2$] and 1.16[m, 24H, CHMe$_2$]. FABMS is fast atom bombardment mass spectrometry.

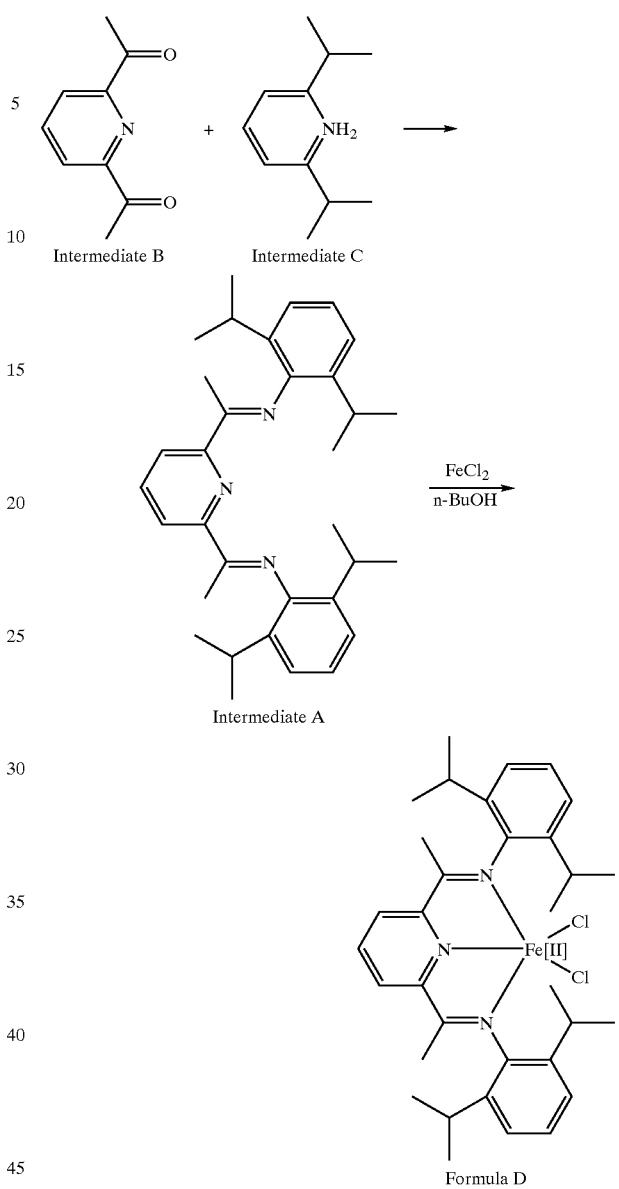

Preparation of the Formula D compound [2,6-diacetylpyridinebis(2,6-diisopropylanil)FeCl$_2$]

FeCl$_2$ (0.24 g; 1.89 mmol) was dissolved in hot n-butanol (20 ml) at 80° C. A suspension of 2,6-diacetylpyridinebis (2,6-diisopropylanil) (0.92 g; 1.89 mmol) in n-butanol was added dropwise at 80° C. The reaction mixture turned blue. After stirring at 80° C. for 15 minutes the reaction was allowed to cool down to room temperature. The reaction volume was reduced to a few ml, and petroleum ether (40/60) was added to precipitate the product (a blue powder), which was subsequently washed three times with 10 ml petroleum ether (40/60). The yield was 0.93 g (81%).

Mass spectrum: m/z 607 [M]+, 572 [M−Cl]+, 482 [M−FeCl$_2$]+.

Analysis—Calculated: for $C_{33}H_{43}N_3FeCl_2$: C, 65.14; H, 7.12; N, 6.91. Found: C, 64.19; H, 6.90; N, 6.70.

Runs 1.1 to 1.6—Polymerisation Tests

The polymerisation tests described in Runs 1.1 to 1.6 were were carried out using the following procedure. The catalyst of Formula D and cocatalyst (methylalumoxane—"MAO") was added to a Schlenk tube and dissolved in toluene (40 ml). The tube was purged with ethylene and the contents were mechanically stirred and maintained under 1 bar ethylene for the duration of the polymerisation. After half an hour the polymerisation was terminated by the addition of aqueous hydrogen chloride. The produced solid polyethylene was filtered off, washed with methanol and dried in a vacuum oven at 50° C. In Run 1.1, some toluene soluble polyethylene was recovered from the filtrate by separating the toluene layer, drying over $MgSO_4$, and evaporating the solvent.

The results of the polymerisation tests are summarised in the following Table.

It will be seen from the Table that the iron compound catalyst provided high activity in the polymerisation of ethylene using methylalumoxane as cocatalyst, but that use of diethylaluminiumchloride as cocatalyst (Run 1.4) gave poor activity. The use of a cocatalyst consisting of a perfluorophenylboron compound with triisobutylaluminium gave moderately high activity.

TABLE

| Example | Catalyst mmol | Cocatalyst/ Quantity (Note 1) | PE solid | PE (soluble) (Note 2) | Activity (Note 3) |
|---|---|---|---|---|---|
| 1.1 | 0.05 | MAO/400 | 12.0 g | 0.78 g | 480 |
| 1.2 | 0.025 | MAO/400 | 8.0 g | nd | 640 |
| 1.3 | 0.025 | MAO/400 | 9.7 g | nd | 780 |
| 1.4 | 0.025 | DEAC/400 | 0.01 g | 0 | low |
| 1.5 | 0.025 | See Note 4 | 3.5 g | 0 | 280 |
| 1.6 | 0.01 | MAO/100 | 5.7 g | nd | 1130 |

Notes on the Table

1. MAO is methylalumoxane (cocatalyst). DEAC is diethylaluminium chloride. The "Quantity" units are milliequivalents based on atoms of aluminium. The MAO was supplied by Aldrich except in Run 1.3 in which the MAO was prepared according to the method provided by Gianetti, E.; Nicoletti, G. M.; Mazzocchi, R. Journal of Polymer Science: Part A; Polymer Chemistry 1985, 23, 2117–2133.
2. Recovered from the toluene reaction medium.
3. The activity is expressed as g $mmol^{-1}$ $h^{-1}$ $bar^{-1}$ (grams of polymer produced per millimole of catalyst per hour per bar pressure of ethylene).
4. In Run 1.5, the cocatalyst was provided by 1 millequivalent of tris(perfluorophenyl)boron and 20 milliequivalents of triisobutylaluminium.

Example 2

The manganese[II] compound illustrated in the following diagram was prepared and tested for catalytic activity in the polymerisation of ethylene.

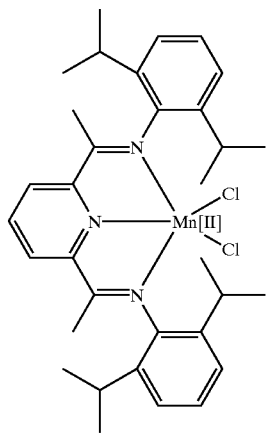

FORMULA J

Preparation of Manganese(II) compound with Formula J [(2,6-diacetylpyridine(2.6-diisopropylanil)$MnCl_2$]

A suspension of $MnCl_2.4H_2O$ (0.50 g, 2.53 mmol) and Intermediate A (1.22 g, 2.53 mmol) was refluxed in acetonitrile (50 ml) for 12 h to give an orange solution. On cooling to room temperature orange crystals were obtained of the Mn(II) compound of Formula J; yield 59%. Microanalysis data supported the Formula J empirical formula. The FAB mass spectrum displayed a highest peak corresponding to an M+−Cl (571) ion.

Polymerisation Test—Run 2.1

A 1.8 M solution of diethylaluminium chloride (DEAC) in toluene (0.50 ml, 0.9 mmol, 30 equivalents) was added via syringe to a stirred suspension of the Formula J Mn(II) compound (18 mg, 0.03 mmol) in toluene (40 ml). The produced catalyst solution was degassed under reduced pressure and back-filled with an atmosphere of ethylene. During the run time of 20 h the solution was left open to a supply of ethylene at one atmosphere and stirred vigorously at 25° C. The polymerisation was terminated by the addition of dilute HCI (ca. 40 ml) and then stirred for 30 minutes to dissolve the alkylaluminium residues. Solid polyethylene was filtered from the reaction, washed with an acidified methanol solution and dried in vacuo at 40° C. overnight. Yield 0.011 g. Activity was 0.2 $gmmol^-$ 1 $hr^-$ 1 $bar^-$1.

Example 3

Preparation of 2,6-diacetylpyridine(2,6-diisopropylanil)$CoCl_2$—Formula K

Cobalt chloride ($CoCl_2$—0.057 g; 0.44 mmol) was dissolved in hot n-butanol (10 ml) at 80° C. A suspension of Intermediate A [2,6-diacetylpyridinebis(2,6-diisopropylanil)] (0.21 g; 0.44 mmol) in n-butanol was added dropwise at 80° C. After stirring at 80° C. for 15 minutes the produced reaction mixture was allowed to cool to room temperature. The reaction volume was reduced to a few ml and petroleum ether (40/60) was added to precipitate the product. The olive green powdery precipitate was washed three times with 10 ml aliquots of petroleum ether (40/60). The yield of the cobalt complex (Formula K—see below) was 0.18 g (67% of theory). The mass spectrum showed m/z 575 $[M-Cl]^+$, 538 $[M-2Cl]^+$ Polymerisation Tests—Runs 3.1 and 3.2

Polymerisation tests were carried out as described in Example 1 except that the catalyst was the Formula K compound. The MAO employed (obtained from Aldrich—Catalogue No. 40,459-4) was a 10 weight % solution in toluene.

It will be seen from the Table that the Formula K catalyst when activated with MAO was highly active in the polymerisation of ethylene.

TABLE

| Example | Catalyst mmol | Cocatalyst/ Quantity (Note 5) | PE solid | Activity (Note 6) |
|---|---|---|---|---|
| 3.1 | 0.05 | MAO/100 | 5.2 g | 207 |
| 3.2 | 0.01 | MAO/100 | 2.3 g | 464 |

Notes on the Table
5. The "Quantity" units are milliequivalents based on atoms of aluminium
6. The activity is expressed as g mmol$^{-1}$ h$^{-1}$ bar$^{-1}$ (grams of polymer produced per millimole of catalyst per hour per bar pressure of ethylene).

FORMULA K

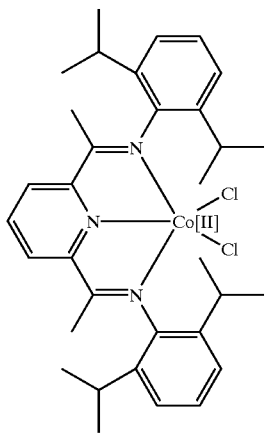

Examples 4 to 9
Preparation of Iron Complexes

Example 4

4.1—Preparation of 2,6-diacetylpyridinebis(2-tert.-butylanil)

To a solution of 2,6-diacetylpyridine (0.54 g; 3.31 mmol) in absolute ethanol (20 ml) was added 2-tertiarybutylaniline (1.23 g; 2.5 eq.). After the addition of 2 drops of acetic acid (glacial) the solution was refluxed overnight. Upon cooling to room temperature the product crystallised from ethanol. The product was filtered, washed with cold ethanol and dried in a vacuum oven (50° C.) overnight. The yield was 1.07 g (76%). Analysis 1H NMR(CDCl$_3$): 8.43, 7.93, 7.44, 7.21, 7.09, 6.56 (m, 7H, ArH, pyrH), 2.43 (s, 6H, N=CCH$_3$), 1.39 (s, 18H, CCH$_3$).

4.2—Preparation of 2,6-diacetylpyridinebis(2-tert.-butylanil)FeCl$_2$

FeCl$_2$ (0.15 g; 1.18 mmol) was dissolved in hot n-butanol (20 ml) at 80° C. A suspension of 2,6-diacetylpyridinebis(2-tert.-butylanil) (0.5 g; 1.18 mmol) in n-butanol was added dropwise at 80° C. The reaction mixture turned blue. After stirring at 80° C. for 15 minutes the reaction was allowed to cool down to room temperature. The reaction volume was reduced to a few ml and diethyl ether was added to precipitate the product as a blue powder, which was subsequently washed three times with 10 ml diethyl ether. The yield was 0.55 g (85%). Analysis—Mass spectrum: m/z 551 [M]+, 516 [M–Cl]+, 426 [M–FeCl$_2$]+.

Example 5

5.1—Preparation of 2,6-diacetylpyridinebis(2-methylanil)

The procedure was as for Example 4.1 except that 2-methyl aniline was used instead of 2-tertiarybutylaniline. The yield was Yield: 0.42 g (33%)

$^1$H NMR(CDCl$_3$): 8.48 (d, 2H, pyrH), 7.91 (t, 1H, pyrH),, 7.28 (m, 4H, ArH), 7.10 (m,2H, ArH), 6.75 (m, 2H, ArH), 2.42 (s, 6H, N=CCH$_3$), 2.20 (s, 6H, CH$_3$).

5.2—Preparation of 2,6-diacetylpyridinebis(2-methylanil)FeCl$_2$

The procedure was as for Example 4.2 except that 2,6-diacetylpyridinebis(2-methylanil) was employed instead of 2,6-diacetylpyridinebis(2-tert.-butylanil). The yield was 77% of theoretical.

Mass spectrum: m/z 467 [M]$^+$, 432 [M–Cl]$^+$.

Example 6

6.1—Preparation of 2,6-diacetylpyridinebis(2,3-dimethylanil)

The procedure was as for Example 4.1 except that 2,3-dimethyl aniline was used instead of 2-tertiarybutylaniline. The yield was 80% of theoretical.

$^1$H NMR(CDCl$_3$): 8.41, 7.89, 7.10, 6.94, 6.55, (m, 9H, ArH, pyrH), 2.33 (m, 6H, N=CCH$_3$, 6H, CCH$_3$), 2.05 (s, 6H, CCH$_3$).

Mass spectrum: m/z 369 [M]$^+$.

6.2—Preparation of 2,6-diacetylpyridinebis(2,3-dimethylanil)FeCl$_2$

The procedure was as for Example 4.2 except that 2,6-diacetylpyridinebis(2,3-dimethylanil) was employed instead of 2,6-diacetylpyridinebis(2-tert.-butylanil). The yield was 83% of theoretical.

Mass spectrum: m/z 496 [M]$^+$, 461 [M–Cl]$^+$, 425 [M–Cl$_2$]$^+$.

Example 7

7.1—Preparation of 2,6-diacetylpyridinebis(2,4-dimethylanil)

The procedure was as for Example 4.1 except that 2,4-dimethyl aniline was used instead of 2-tertiarybutylaniline. The yield was 75% of theoretical.

$^1$H NMR(CDCl$_3$): 8.41, 7.90, 7.05, 6.90, 6.55, (m, 9H, ArH, pyrH), 2.36 (m, 6H, N=CCH$_3$, 6H, CCH$_3$), 2.13 (s, 6H, CCH$_3$).

Mass spectrum: m/z 369 [M]$^+$.

7.2—Preparation of 2,6-diacetylpyridinebis(2,4-dimethylanil)FeCl$_2$

The procedure was as for Example 4.2 except that 2,6-diacetylpyridinebis(2,4-dimethylanil) was employed instead of 2,6-diacetylpyridinebis(2-tert.-butylanil). The yield was 75% of theoretical.

Mass spectrum: m/z 496 [M]+, 461 [M–Cl]+, 425 [M–Cl$_2$]+.

Example 8

8.1—Preparation of 2,6-diacetylpyridinebis(2,6-dimethylanil)

The procedure was as for Example 4.1 except that 2,6-dimethyl aniline was used instead of 2-tertiarybutylaniline. The yield was 78% of theoretical.

$^1$H NMR(CDCl$_3$): 8.48, 8.13, 7.98, 7.08, 6.65, (m, 9H, ArH, pyrH), 2.25 (s, 6H, N═CCH$_3$), 2.05 (m, 12H, CCH$_3$).

Mass spectrum: m/z 369 [M]+.

8.2—Preparation of 2,6-diacetylpyridinebis(2,6-dimethylanil)FeCl$_2$

The procedure was as for Example 4.2 except that 2,6-diacetylpyridinebis(2,6-dimethylanil) was employed instead of 2,6-diacetylpyridinebis(2-tert.-butylanil). The yield was 78% of theoretical.

Mass spectrum: m/z 496 [M]+, 461 [M–Cl]+, 425 [M–Cl$_2$]+.

Example 9

9.1—Preparation of 2,6-diacetylpyridinebis(2,4,6-trimethylanil)

The procedure was as for Example 4.1 except that 2,4,6-trimethyl aniline was used instead of 2-tertiarybutylaniline. The yield was 60% of theoretical.

$^1$H NMR(CDCl$_3$): 8.50, 7.95, 6.94, (m, 7H, ArH, pyrH), 2.33 (s, 6H, N═CCH$_3$), 2.28 (s, 6H, CCH$_3$), 2.05 (s, 12H, CCH$_3$).

Mass spectrum: m/z 397 [M]+.

9.2—Preparation of 2,6-diacetylpyridinebis(2,4,6-trimethylanil)FeCl$_2$

The procedure was as for Example 4.2 except that 2,6-diacetylpyridinebis(2,4,6-trimethylanil) was employed instead of 2,6-diacetylpyridinebis(2-tert.-butylanil). The yield was 64% of theoretical.

Mass spectrum: m/z 523 [M]+, 488 [M–Cl]+, 453 [M–Cl$_2$]+.

Examples 4 to 9

Polymerisation Tests on Iron Complexes

The polymerisation tests were carried out using the following procedure. The catalysts (iron complexes) prepared in each of Examples 4 to 9 and cocatalyst (methylalumoxane—"MAO") was added to a Schienk tube and dissolved in toluene (40 ml). The "MAO" was used as a 10 wt % solution in toluene (supplied by Aldrich, catalogue number: 40,459-4). The tube was purged with ethylene and the contents were mechanically stirred and maintained under 1 bar ethylene for the duration of the polymerisation. The polymerisation tests were each commenced at room temperature (20° C.). After half an hour the polymerisation was terminated by the addition of aqueous hydrogen chloride. The produced solid polyethylene was filtered off, washed with methanol and dried in a vacuum oven at 50° C. The toluene soluble fraction (PE tol. sol.) was isolated from the filtrate by separation of the toluene layer from the aqueous layer, drying over MgSO$_4$ and removal of the toluene by distillation. GC/MS analysis showed that the toluene soluble fraction consists of oligoineric products.

The results of the polymerisation tests are summarised in the Table 3.

TABLE 3

| Complex from Example No. | Catalyst mmol | Cocatalyst/ equivalents | PE solid grams | PE tol. sol. grams | Activity g/mmolhbar |
|---|---|---|---|---|---|
| 4.2 | 0.01 | MAO/100 | 5.01 | — | 1002 |
| 5.2 | 0.01 | MAO/100 | | 0.32 | 64 |
| 6.2 | 0.02 | MAO/400 | 0.26 | 2.63 | 289 |
| 7.2 | 0.02 | MAO/400 | | 1.20 | 120 |
| 8.2 | 0.02 | MAO/400 | 5.7 | | 566 |
| 9.2 | 0.01 | MAO/100 | 6.2 | | 1230 |

Analysis for Solid Polyethylene

| Example No. | Mn | Mw | PDI |
|---|---|---|---|
| 4.2 | 4100 | 228000 | 55.3 |
| 6.2 | 620 | 910 | 1.5 |
| 8.2 | 1900 | 29000 | 15.3 |
| 9.2 | 4400 | 52000 | 11.9 |

Analysis for Toluene Soluble Polyethylene

| Example No | Mn | Mw | PDI |
|---|---|---|---|
| 6.2 | 300 | 410 | 1.4 |

Example 10

10.0—Preparation of 2,6-pyridinedicarboxaldehyde 2,6-Dimethanolpyridine (5.55 g, 0.040 mol—supplied by Aldrich Chemical Co.) and selenium dioxide (4.425 g, 0.040 mol, 1 equivalent) were dissolved in 1,4-dioxane (100 ml) and refluxed (4 h). The resulting mixture was filtered to yield a clear orange solution. The solvent was removed under vacuum and the product was recrystallised from chloroform-:petroleum ether (40/60° C.) 1:1) to yield a white powder (7.44 g, 75%)

Analysis—Mass spectrum (CI) 136 [M+H]+, 153 [M+NH3]+

$^1$H NMR (250 Hz, CDCl$_3$) 10.17 (2H, s), 8.19 (2H, d, J=8.4 Hz), 8.17 (1H, t, J=8.4 Hz)

10.1—Preparation of 2,6-dialdiminepyridinebis(2,6-dimethylanil)

To the 2,6-pyridinedicarboxaldehyde (0.80 g, 5.93 mmol), prepared as described above, in absolute ethanol (50 ml), was added redistilled 2,6-dimethylaniline (2.1 eq, 12.45 mmol, 1.5 ml) and glacial acetic acid (catalytic, 3 drops) and the resulting mixture was refluxed (24 h). Cooling and recrystallisation (absolute ethanol) yielded a yellow powder, (1.654 g, 82%). Analysis Mass spectrum (CI) 342 [M+H]+

$^1$H NMR (250 Hz, CDCl3) 8.43 (2H,s), 8.40(2H,d, J=7.6 Hz), 8.00 (1H,t,7.6J), 7.10 (4H,d,J=7.4 Hz), 6.99 (2H,t,J=7.4 Hz), 2.20 (12H,s)

$^{13}$NMR (250 Hz, CDCl3) 163.17, 154.45, 150.26, 137.32, 128.16, 126.77, 124.39, 122.68, 18.31

10.2—Preparation of 2,6-dialdiminepyridinebis(2,6-dimethylanil)FeCl$_2$

To FeCl$_2$ (0.127 g, 1.0 mmol) dissolved in hot, dry, n-butanol (40 ml) at 80° C., a suspension of 2,6-dialdiminepyridinebis(2,6-dimethylanil) (0.341 g, 1.0 mmol, 1 eq) in hot, dry, n-butanol (10 ml) was added dropwise at 80° C. The reaction mixture turned green. After stirring for 15 mins at 80° C. the mixture was allowed to cool to room temperature and stirred for a further 12 h. The reaction solvent volume was reduced to approximately 1 ml and the reaction mixture was washed with diethyl ether (3×40 ml) to yield a light green powder (0.279 g, 60%). Mass spectrum (FAB+) m/z: 467 [M]+, 432 [M−Cl]+

Example 11

11.1—Preparation of 2,6-dialdiminepyridinebis(2,6-diethylanil)

To 2,6-pyridinedicarboxaldehyde (0.169 g, 1.25 mmol) prepared as described in Example 10.0 above, in absolute ethanol (25 ml), was added redistilled 2,6-diethylaniline (2.1 eq, 2.63 mmol, 0.36 ml) and glacial acetic acid (catalytic, 1 drop). The resulting mixture was refluxed (24 h). Cooling and recrystalisation (absolute ethanol) yielded a yellow powder, (0.371 g, 75%). Analysis—Mass spectrum (CI) 398 [M+H]+ $^1$H NMR (250 Hz, CDCl3) 8.44 (2H,s), 8.40 (2H,d,J=7.6 Hz), 8.00 (1H,t,J=7.6 Hz), 7.25 (6H,M), 2.55 (8H,q,J=7.5 Hz), 1.61 (12H,t,J=7.5 Hz)

11.2—Preparation of 2,6-dialdiminepyridinebis(2,6-diethylanil) FeCl$_2$

To FeCl$_2$ (0.076 g, 0.6 mmol) dissolved in hot, dry, n-butanol (40 ml) at 80° C., a suspension of 2,6-dialdiminepyridinebis(2,6-diethylanil) (0.240 g, 0.6 mmol, 1 eq) in hot, dry, n-butanol (10 ml) was added dropwise at 80° C. The reaction mixture turned dark green. After stirring for 15 mins at 80° C. the mixture was allowed to cool to room temperature and stirred for a further 12 h. The reaction solvent volume was reduced to approximately 1 ml and the reaction mixture was washed with diethyl ether (3×40 ml), to yield a dark green powder, (0.238 g,76%). Analysis—Mass spectrum (FAB+) m/z: 523 [M]+, 488 [M−Cl]+, 453 [M−Cl2]+, 398 [M−FeCl2]+

Example 12

12.1—Preparation of 2,6-dialdiminepyridinebis(2,6-diisopropylanil)

To 2,6-pyridinedicarboxaldehyde (0.101 g, 0.75 mmol) prepared as described in Example 10.0 above, in absolute ethanol (20 ml), was added redistilled 2,6-diisopropylaniline (2.1 eq, 1.57 mmol, 0.26 ml) and glacial acetic acid (catalytic, 1 drop). The resulting mixture was refluxed (24 h). Cooling and recrystallisation (absolute ethanol) yielded a yellow powder, (0.270 g, 80%). Analysis—Mass spectrum (CI) 454 [M+H]+

$^1$H NMR (250 Hz, CDCl3) 8.44 (2H,s), 8.40 (2H,d,J=7.6 Hz), 8.00 (1H,t,J=7.6 Hz), 7.23 (6H,M), 3.01 (4H,sept.,J =6.9 Hz), 1.21 (24H,d,J =6.9 Hz)

$^{13}$C NMR (250 Hz, CDCl3) 163.52, 162.69, 154.43, 148.30, 137.36, 137.14, 123.05, 122.76, 27.99, 23.44.

12.2—Preparation of 2,6-dialdiminepyridinebis(2,6-diisopropvlanil)FeCl$_2$

To FeCl$_2$ (0.070 g, 0.55 mmol) dissolved in hot, dry, n-butanol (40 ml) at 80° C., a suspension of 2,6-dialdiminepyridinebis(2,6-diisopropylanil) (0.245 g, 0.55 mmol, 1 eq) in hot, dry, n-butanol (10 ml) was added dropwise at 80° C. The reaction mixture turned dark green. After stirring for 15 mins at 80° C. the mixture was allowed to cool to room temperature and stirred for a further 12 h. The reaction solvent volume was reduced to approximately 1 ml and the reaction mixture was washed with diethyl ether (3×40 ml), to yield a dark green powder, (0.205 g,65%). Analysis—Mass spectrum (FAB+) m/z: 576 [M]+, 544 [M−Cl]+, 454 [M−FeCl$_2$]+

Example 13

13.1—Preparation of 2,6-dialdiminepyridinebis(1-naphthil)

To 2,6-pyridinedicarboxaldehyde (0.658 g, 4.81 mmol) ) prepared as described in Example 10.0 above, in absolute ethanol (40 ml), was added 1-aminonaphthalene (2.1 eq, 10.10 mmol, 1.448 g) and glacial acetic acid (catalytic, 1 drop). The resulting mixture was refluxed (24 h). Cooling and recrystallisation (absolute ethanol) yielded a yellow powder, (1.48 g, 80%). Analysis—Mass spectrum (EI) 385 [M]+

13.2—Preparation of 2,6-dialdiminepyridinebis(1-naphthil)FeCl$_2$

To FeCl$_2$ (0.20 g, 1.57 mmol) dissolved in hot, dry n-butanol (80 ml) at 80° C., a suspension 2,6-dialdiminepyridinebis(1-naphthil) (0.610 g, 1.57 mmol, 1 eq) in hot, dry, n-butanol (25 ml) was added dropwise at 80° C. The reaction mixture turned green. After stirring for 15 mins at 80° C. the mixture was allowed to cool to room temperature and stirred for a further 12 h. The reaction solvent volume was reduced to approximately 1 ml and the reaction mixture was washed, with diethyl ether (3×40 ml) to yield a green powder, (0.57 g,71%). Analysis—Mass spectrum (FAB+) m/z: 511 [M]+, 476 [M−Cl]+, 441[M−Cl$_2$]+, 386 [M−FeCl$_2$]+

Examples 10 to 13

Polymerisation Tests

The iron complexes prepared in Examples 10 to 13 were tested in polymerisation of ethylene under the following standard conditions. To the iron complex (0.01 mmol), dissolved in toluene (40 ml, dry) in a Schlenk tube, the cocatalyst (methylaluminoxane—'MAO') was added (0.065 ml, 10 wt % in toluene, 100 eq (Fe:Al=1:100)) to produce an orange solution. The Schlenk tube was placed in a water bath, purged with ethylene and the contents magnetically stirred and maintained under 1 bar ethylene for the duration of the polymerisation. After 30 minutes the polymerisation was terminated by the addition of aqueous hydrogen chloride. The insoluble, solid, polyethylene was recovered by filtration, washed with methanol (50 ml) and dried (vacuum oven at 50° C.). The toluene solution was dried over MgSO$_4$, and the solvent removed under vacuum to yield traces of waxy material. GC-MS of the toluene solution showed the waxy material to consist of α-olefins (vinyl terminated oligomeric hydrocarbons). The results of the polymerisation tests are shown in the following Table.

TABLE

| Iron complex Example No. | Cocatalyst/ eq (note 1) | Solid PE/g | Soluble PE (note 2) | MW solid PE | Activity/ g mmol$^{-1}$ bar$^{-1}$h$^{-1}$ |
|---|---|---|---|---|---|
| 10 | MAO | 3.618 | 0.085 | 15000 | 740 |
| 11 | MAO | 2.984 | 0.261 |  | 649 |
| 12 | MAO | 4.803 | 0.038 | 33000 | 968 |
| 13 | MAO | 0.450 | 0.601 | 900 | 210 |

Notes on the Table
1) MAO obtained from the Aldrich Chemical Co
2) Recovered from the reaction medium. In Example 13 the Mw of the soluble PE (polyethylene) was 300.

Examples 14 to 25

These Examples are a series of tests wherein ethylene or ethylene/1-hexene is polymerised under 10 bars ethylene pressure using the catalysts of the present invention under "slurry" polymerisation conditions.

Catslyst Preparation

The transition metal complexes employed as catalyst in Examples 14 to 25 were as follows:

In Examples 14 and 15 the complex was 2,6-diacetylpyridinebis(2,6-diisopropylanil)FeCl$_2$ prepared as described in Example 1 (Formula D compound).

In Examples 16 to 20 the complex was was 2,6-diacetylpyridinebis(2,6-dimethylanil)FeCl$_2$ prepared as described in Example 8.

In Example 21 the complex was 2,6-diacetylpyridinebis (2,4-dimethylanil)FeCl$_2$ prepared as described in Example 7.

In Examples 22 to 24 the complex was 2,6-diacetylpyridinebis(2,4,6-trimethylanil)FeCl$_2$ prepared as described in Example 9.

In Example 25 the complex was 2,6-diacetylpyridinebis (2,6-diisopropylanil)CoCl$_2$ prepared as described in Example 3 (Formula K).

Catalyst Activation

The transition metal complex was dissolved in toluene (previously dried over sodium metal) under a nitrogen atmosphere and there was added a solution of activator (cocatalyst) at ambient temperature. The mixture was stirred at room temperature then an aliquot transferred to the injection unit of a polymerisation reactor. The quantities of reagents employed in the catalyst activation are set out in the following Table. All operations were conducted under a nitrogen atmosphere unless specified. "MAO" is methyl aluminoxane (1.78M in toluene supplied by Witco). "MMAO" is modified methyl aluminoxane (10% w/w in heptane—supplied by Witco) were used as purchased. Tri-isobutylaluminium (Al(iBu)$_3$ as a 1M solution in toluene was supplied by Aldrich.

TABLE

| Ex. No. | Metal Complex (mg) | [Metal] (μmols) | Cocatalyst type | Cocatalyst (ml) | [Al] mmols | [M]:[Al] | Toluene (ml) | Solution Molarity (M) |
|---|---|---|---|---|---|---|---|---|
| 14 | 3 | 5 | MAO | 2.78 | 5 | 1:1000 | 20 | 0.0025 |
| 15 | 3 | 5 | MAO | 2.78 | 5 | 1:1000 | 20 | 0.0025 |
| 16 | 1.5 | 3 | MAO | 1.70 | 5 | 1:1000 | 10 | 0.0025 |
| 17 | 1.5 | 3 | MMAO | 3.93 | 3 | 1:1000 | 10 | 0.0025 |
| 18 | 1.5 | 3 | MAO | 1.70 | 3 | 1:1000 | 50 | 0.0006 |
| 19 | 1.5 | 3 | MAO | 1.70 | 3 | 1:1000 | 10 | 0.0025 |
| 20 | 1.5 | 3 | MAO | 0.17 | 3 | 1:1000 | 10 | 0.0025 |
| 21 | 1.5 | 3 | MAO |  | 3 | 1:1000 | 10 | 0.0025 |
| 22 | 3 | 6 | MAO | 3.22 | 6 | 1:1000 | 20 | 0.003 |
| 23 | 1.5 | 3 | MAO | 1.61 | 3 | 1:1000 | 10 | 0.003 |
| 24 | 3 | 6 | MAO | 0.32 | 0.3 | 1:100 | 20 | 0.003 |
| 25 | 3 | 5 | MAO | 2.78 | 5 | 1:1000 | 20 | 0.0025 |

Polymerisation Tests

The reagents used in the polymerisation tests were Ethylene Grade 3.5 (supplied by Air Products), hexene (supplied by Aldrich) distilled over sodium/nitrogen and triisobutylaluminium (1M in hexanes, supplied by Aldrich).

Polymerisation of Ethylene

A 1 liter reactor was baked out under a nitrogen flow for at least 1 hour at >85° C. The reactor was then cooled to 50° C. Isobutane (0.5 liter) and triisobutylaluminium were then added and the reactor was boxed in nitrogen. The alkyl aluminium was allowed to scavenge for poisons in the reactor for at least 1 hour. Ethylene was introduced into the reactor until a predetermined over-pressure was achieved then the catalyst solution was injected under nitrogen. The reactor pressure was maintained constant throughout the polymerisation run by computer controlled addition of additional ethylene. The polymerisation time was 1 hour. Upon termination of the run the reactor contents were isolated, washed with acidified methanol (50 ml HCl/2.5l methanol) and water/ethanol (4:1 v/v) and dried under vacuum, at 40° C, for 16 hours.

Copolymerisation of Ethylene/1-Hexene (Example 19)

A 1 liter reactor was baked out under a nitrogen flow for at least 1 hour at >85° C. The reactor was then cooled to 50° C, isobutane (0.5 liter), 1-hexene and triisobutylaluminium were then added and the reactor was boxed in nitrogen. The alkyl aluminium was allowed to scavenge for poisons in the reactor for at least 1 hour. Ethylene was introduced into the reactor until a predetermined over-pressure was achieved then the catalyst solution was injected under nitrogen. The reactor pressure was maintained constant throughout the polymerisation run by computer controlled addition of ethylene. The polymerisation time was 40 minutes. Upon termination of the run the reactor contents were isolated, washed with acidified methanol (50 ml HCl/2.51 methanol) and water/ethanol (4:1 v/v) and dried under vacuum, at 40° C., for 16 hours.

Data from the polymerisation tests are set out below in the Table

Example 26

Preparation of the Supported Catalyst 2,6-Diacetylpyridinebis(2,6-diisopropylanil)$FeCl_2$ was prepared as described in Example 1.

Silica (1.03g ES70, supplied by Crosfield), which had been heated under flowing nitrogen at 700° C., was placed in a Schlenk tube, and toluene (10 ml) was added. The mixture was heated to 50° C. To a solution of 2,6-diacetylpyridinebis(2,6-diisopropylanil)$FeCl_2$ (0.036g) in toluene (10 ml) was added methylaluminoxane (5 ml, 1.78M in toluene, supplied by Witco). This mixture was heated at 50° C. and then transferred to the silica/toluene mixture. The silica/MAO/toluene mixture was maintained at 50° C., with regular stirring, for 1 hour before the toluene was removed, at 65° C., under vacuum to yield a free flowing powder.

TABLE

| Ex. No. | [metal] ([mols) | metal/aluminoxane Ratio | $C_2H_4$ Bar | $Al(iBu)_3$ (ml) | polymerisation Temp. (° K.) | polymer (g) | activity (g/mmol M/h/b) | ppm |
|---|---|---|---|---|---|---|---|---|
| 14 | 0.5 | 1:1000 | 10 | 3 | 323 | 26.9 | 5430 | 1.03 |
| 15 | 0.5 | 1:1000 | 10 | 3 | 298 | 45.0 | 9090 | 0.61 |
| 16 | 0.6 | 1:1000 | 10 | 3 | 323 | 56.5 | 9340 | 0.60 |
| 17 | 0.6 | 1:1000 | 10 | 3 | 323 | 57.4 | 9510 | 0.59 |
| 18 | 0.12 | 1.1000 | 10 | 3 | 323 | 3.3 | 2540 | 2.2 |
| 19# | 0.6 | 1:1000 | 10# | 3 | 323 | 67.6 | 16690 | 0.50 |
| 20 | 0.6 | 1:1000 | 10 | 3 | 323 | 74.5 | 12310 | 0.45 |
| 21 | 0.6 | 1:1000 | 10 | 3 | 323 | 7.8 | 1280 | 4.36 |
| 22 | 0.6 | 1:1000 | 10 | 3 | 323 | 63.1 | 11020 | 0.51 |
| 23 | 0.12 | 1:1000 | 10 | 3 | 323 | 55.7 | 48690 | 0.11 |
| 24 | 0.6 | 1:100 | 2 | 2 | 323 | 18.21 | 15150 | 18.4 |
| 25 | 0.8 | 1:1000 | 10 | 3 | 323 | 3.7 | 450 | 13.1 |

Notes on the Table

\# Example 19 illustrated copolymerisation of ethylene with 1-hexene. 1-Hexene (50 ml) was included in the polymerisation. The remaining Examples were all homopolymerisation of ethylene.

"pp" is defined as parts by weight of transition metal per million parts by weight of polymer.

Molecular weight data of the polymers obtained from Examples 14 to 25 are set out in the Table below.

TABLE

| Ex. No. | Mw | Mn | Mpeak | PD |
|---|---|---|---|---|
| 14 | 611000 | 64000 | 246000 | 9.5 |
| 15 | 857000 | 212000 | 451000 | 4.0 |
| 16 | 242000 | 9600 | 16000 | 25.3 |
| 17 | 278000 | 5700 | 1300 | 48.7 |
| 18 | 366000 | 50000 | 102000 | 7.3 |
| 19 | 377000 | 6500 | 43000 | 57.7 |
| 21 | 470 | 360 | 370 | 1.3 |
| 25 | 14000 | 4200 | 12000 | 3.3 |

Examples 26 and 27

Gas Phase Polymerisation Tests with Supported Catalysts

Examples 26 and 27 illustrate the use of the catalysts of the present invention supported on silica support material. Example 26 employs 2,6-diacetylpyridinebis(2,6-diisopropylanil)$FeCl_2$, and Example 27 employs 2,6-diacetylpyridinebis(2,4,6-trimethylanil)$FeCl_2$ as the transition metal complex compound.

Example 27

Preparation of the Supported Catalyst 2,6-Diacetylpyridinebis(2,4,6-trimethylanil)$FeCl_2$ was prepared as described in Example 9. Silica (1.38 g ES70, supplied by Crosfield), which had been heated under flowing nitrogen at 700° C., was placed in a Schlenk tube and toluene (10 ml) was added.

To a solution of 2,6-diacetylpyridinebis(2,4,6-trimethylanil)$FeCl_2$ (0.041 g) in toluene (10 ml) was added methylaluminoxane (13.2 ml, 1.78M in toluene, supplied by Witco). This mixture was heated at 40° C. for 30 minutes to dissolve as much of the iron complex as possible. The solution was then transferred to the silica/toluene. The silica/MAO/toluene mixture was maintained at 40° C., with regular stirring, for 30 minutes before the toluene was removed, at 40° C., under vacuum to yield a free flowing powder. Analysis of the solid gave 16.9% w/w Al and 0.144% w/w Fe.

Polymerisation Tests—Examples 26 and 27

The reagents used in the polymerisation tests were hydrogen Grade 6.0 (supplied by Air Products): ethylene Grade 3.5 (supplied by Air Products): hexene (supplied by Aldrich) distilled over sodium/nitrogen: dried pentane (supplied by Aldrich): methylaluminium (2M in hexanes, supplied by Aldrich): and triisobutylaluminium (1M in hexanes, supplied by Aldrich).

A 3 liter reactor was baked out under flowing nitrogen for at least 1 hour at 77–85° C. before powdered sodium chloride (300 g, predried under vacuum, 160° C., >4 hours) was added. The sodium chloride was used as a fluidisable/stirrable start-up charge powder for the gas phase polymerisation. Trimethyl aluminium (3 ml, 2M in hexanes) was added to the reactor and was boxed in nitrogen. The alkyl aluminium was allowed to scavenge for poisons in the reactor for between ½–1 hour before being vented using 4×4 bar nitrogen purges. The gas phase composition to be used for the polymerisation was introduced into the reactor and preheated to 77° C. prior to injection of the catalyst composition. The catalyst (0.18–0.22 g) was injected under nitrogen and the temperature then adjusted to 80° C. The ratio of hexene and/or hydrogen to ethylene during the polymerisation was kept constant by monitoring the gas phase composition by mass spectrometer and adjusting the balance as required. The polymerisation tests were allowed to continue for between 1 to 2 hours before being terminated by purging the reactants from the reactor with nitrogen and reducing the temperature to <30° C. The produced polymer was washed with water to remove the sodium chloride, then with acidified methanol (50 ml HCl/2.5L methanol) and finally with water/ethanol (4:1 v/v). The polymer was dried under vacuum, at 40° C., for 16 hours. Several Runs, using a variety of operating conditions were carried out with each of the catalysts of Examples 26 and 27. All the polymerisation tests were carried out at a polymerisation temperature of 80° C. and at an ethylene pressure of 8 bars. The polymerisation conditions are set out in the following Table The polymer obtained in Example 27.7 contained short chain branching (SCB) corresponding to 1.6 n-butyl branches/1000 C.

Example 28

28.0—Preparation of 2,6-dialdiminepyridinebis(2,4,6-trimethylanil)

2,6-dimethanolpyridine (6.53 g, 0.048 mol) in absolute ethanol (50 ml), 2,4,6-trimethylaniline (2.5 equivalents, 17.0 ml, 0.12 mol) and glacial acetic acid (3 drops) were mixed together and refluxed for 24 hours. On cooling the mixture, yellow crystals of 2,6-dialdiminepyridinebis(2,4,6-trimethylanil) were separated out (14.28 g, 80% yield).

Analysis of the crystalline product by $^1$H NMR: (250 Hz) 8.42(s, 2H), 8.40 (s, 2H), 8.0(t,$^3$J(H) 8, JH), 7.0(s, 4H), 2.33(s, 6H), 2.19(s, 12H).

Mass spectrum: m/z 369 [M]$^+$.

28.1—Preparation of 2,6-dialdiminepyridinebis(2,4,6-trimethylanil)FeCl$_3$ (Formula G)—see below FeCl$_3$ (0.10 g; 0.615 mmol) was dissolved in MeCN (25 ml) at room temperature and 2,6-dialdiminepyridinebis(2,4,6-trimethylanil) (0.227 g, 0.615 mmol) added. After 24 hours stirring at room temperature a red precipitate of 2,6-dialdiminepyridinebis(2,4,6-trimethylanil)FeCl$_3$ (0.192 g, 60%) was collected and dried. Analysis of the product: Mass spectrum: m/z 531 [M]$^+$, 496 [M–Cl]$^+$, 462[M–2Cl]$^+$.

28.2—Polymerisation Test

The 2,6-dialdiminepyridinebis(2,4,6-trimethylanil)FeCl$_3$ (0.02 mmol) prepared as above was dissolved in toluene (40

TABLE

| Ex/Run | Metal (% w/w) | MAO/Metal Ratio | other cocatalyst/ (mmols) | H$_2$ (bar) | hexane (bar) | pentane (bar) | Run time (min) | Activity, g/mmol M/h/b |
|---|---|---|---|---|---|---|---|---|
| 26.1 | 0.21 | 150 | **** | **** | **** | **** | 75 | 77 |
| 26.2 | 0.21 | 150 | **** | **** | 0.195 | **** | 90 | 77 |
| 26.3 | 0.21 | 150 | TMA/6 | **** | **** | **** | 60 | 149 |
| 26.4 | 0.21 | 150 | TMA/6 | 0.75 | **** | **** | 60 | 318 |
| 27.1 | 0.144 | 300 | **** | **** | **** | **** | 60 | 611 |
| 27.2 | 0.144 | 300 | TMA/6 | 0.5 | **** | **** | 60 | 832 |
| 27.3 | 0.144 | 300 | TMA/6 | 0.5 | 0.2 | **** | 60 | 1054 |
| 27.4 | 0.144 | 300 | TMA/6 | 0.5 | **** | 2.4 | 60 | 1800 |
| 27.5 | 0.144 | 300 | TiBA/3 | **** | **** | **** | 60 | 713 |
| 27.6 | 0.144 | 300 | **** | 3 | **** | **** | 60 | 501 |
| 27.7 | 0.144 | 300 | **** | **** | 0.86 | **** | 60 | 418 |

Molecular weight data on the polymer products is set out in the Table below.

| Run | Catalyst | Mw | Mn | Mpeak | Polydispersity |
|---|---|---|---|---|---|
| 26.2 | Ex 26 | 892000 | 106000 | 332000 | 8.4 |
| 26.3 | Ex 26 | 278000 | 8400 | 95000 | 33.0 |
| 26.4 | Ex 26 | 195000 | 7200 | 43000 | 27.0 |
| 27.1 | Ex 27 | 324000 | 9300 | 134000 | 34.6 |
| 27.2 | Ex 27 | 223000 | 18000 | 42000 | 12.3 |
| 27.3 | Ex 27 | 77000 | 6000 | 21000 | 12.8 |
| 27.4 | Ex 27 | 154000 | 5700 | 28000 | 26.9 |
| 27.5 | Ex 27 | 207000 | 4800 | 86000 | 43.1 |
| 27.6 | Ex 27 | 69000 | 5400 | 14000 | 12.7 |
| 27.7 | Ex 27 | 127000 | 14000 | 51000 | 9.3 | ml) in a Schlenck tube, to give a red solution and the cocatalyst (methylalumoxane), MAO) (8,0 mmol, 400 equiv.) introduced (formation of a orange solution was observed). The MAO was supplied by Aldrich (catalogue number: 40,459-4). The tube was purged with ethylene and the contents stirred under 1 bar ethylene for the duration of the polymerisation. The run was stopped after 0.5 hour by adding aqueous HCl solution. Solid polyethylene (1.5 g) was collected by filtration, washed with methanol and dried in a vacuum oven at 50° C. Polyethylene soluble in the toluene was isolated from the filtrate by separation of the toluene layer from the aqueous layer, drying over MgSO$_4$ and removal of the toluene by distillation. The weight of toluene-soluble polyethylene obtained was 2.46 g. The catalyst activity (based on the total weight of polyethylene obtained) was 396 g mmol$^{-1}$ h$^{-1}$ bar$^{-1}$.

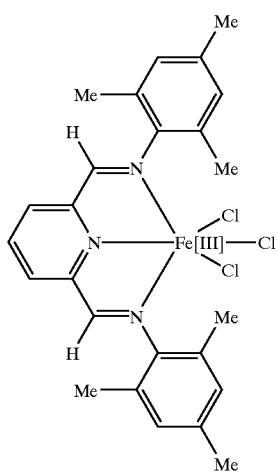

Formula G

Example 29

Preparation of a catalyst from 2,6-diacetylpyridinebis(2,4,6-trimethylanil FeCl$_2$ 2,6-diacetylpyridinebis(2,4,6-trimethylanil)FeCl$_2$ prepared as described in Example 9. To 2,6-diacetylpyridinebis(2,4,6-trimethylanil)FeCl$_2$ (17 mg, 0.03 mmol) dissolved in Et$_2$O (20 ml), at −78° C., was added dropwise a solution of trimethylsilylmethyl magnesium chloride(0.164 mmol, 1M solution in Et$_2$O). The solution was stirred for 10 minutes then allowed to warm to 0° C. and stir for a further 5 minutes. The reaction solvent was removed under reduced pressure. To the iron complex was added trityltetra (pentafluorophenyl)borate(151 mg, 0.164 mmol) and toluene (20 ml, dried) yielding a red solution. The Schlenk tube was purged with ethylene and the contents magnetically stirred and maintained under 1 bar ethylene for the duration of the polymerisation. After 60 minutes the polymerisation was terminated by addition of acidified methanol (50 ml HCl/2.5 L methanol). The insoluable, solid, polyethylene was recovered by filtration, washed with methanol/water (1:4 v/v) and dried (vacuum oven at 40° C.). Yield of solid polyethylene 0.90 g, a polymerisation activity of 28 gmmol$^{-1}$ bar$^{-1}$ h$^{-1}$.

Reagents used in Example 29 were as follows:
Trimethylsilylmethyl magnesium chloride(purchased from Aldrich as a 1M solution in Et$_2$O)
Trityltetra(pentafluorophenyl)borate (purchased from Boulder)
Diethylether (purchased from Aldrich, dried over sodium)
Toluene (purchased from Aldrich, dried over sodium)

Examples 30 and 31

In these Examples, iron (II) complexes comprising tridentate pyridine-hydrazone ligands in accordance with the present invention were synthesised and tested as olefin polymerisation catalysts.

30.1—Preparation of 2,6-bis(1-methyl, 1-phenylhydrazone)pyridine 2,6-diacetylpyridine (5.0 g, 30.6 mmol) [Aldrich Chemicals] and 1-methyl, 1-phenylhydrazine (7.21 ml, 61.3 mmol) [Aldrich Chemicals] in absolute ethanol were stirred together and then heated to reflux for 12 hours. On reducing the volume of the solution by evaporating some of the ethanol and cooling to −20° C., yellow needles of 2,6-bis(1-methyl,1-phenylhydrazone)pyridine were obtained which were filtered off. Yield ca 90%. Mass spectrum:m/z. M$^+$372. Analysis by $^1$H NMR (300 MHz, CDCl$_3$, 298K) δ:2.52 (s, 6H, CH$_3$C=N), 3.32 (s, 6H, CH$_3$—N), 6.95–8.31 (multiplets, 13H, aryls).

30.2—Preparation of 2,6-bis(1-methyl, 1-phenylhydrazone)pyridine.FeCl$_2$ complex FeCl$_2$.4H$_2$O (0.21 g; 1.06 mmol) and 2,6-bis(1-methyl, 1-phenylhydrazone)pyridine (0.39 g; 1.06 mmol) were stirred together in anhydrous n-butanol (10 ml) and heated at 80° C. for 2 hours. The reaction was then allowed to cool down to room temperature. Removal of volatiles in-vacuo, extraction into warm MeCN (30 ml) and cooling (−20° C.) afforded the desired iron complex (Formula L below) as large brown needles. Yield ca 85%.

31.1—Preparation of 2,6-bis(1,1-diphenylhydrazone)pyridine

This compound was prepared in analogous manner to that outlined in Example 30.1 using 2,6-diacetylpyridine (1.0 g, 6.13mol) and 1,1-diphenylhydrazine hydrochloride (2.7 g, 12.3 mmol) [Aldrich Chemicals]. Yield ca 85%. Analysis by $^1$H NMR (300 MHz, CDCl$_3$, 298K) δ:2.12 (s, 6H, CH$_3$C=N), 7.09–8.35 (multiplets, 23H, aryls).

31.2—Preparation of 2,6-bis(1,1-diphenylhydrazone)pyridine.FeCl$_2$ complex This complex (see Formula M below) was prepared by an analogous manner to that outlined in Example 30.2 from FeCl$_2$.4H$_2$O (0.5 g, 2.51 mmol) and 2,6-bis(1,1-diphenylhydrazone)pyridine (1.19 g, 2.52 mmol). Yield ca 70%

Mass spectrum:ny/z M$^+$−Cl 586.

30.3 and 30.4—Polymerisation Tests

The iron complexes prepared in Examples 30.2 and 31.2 were tested in polymerisation of ethylene under the following standard conditions. To the iron complex, dissolved in toluene (40 ml, dried over sodium wire) in a Schlenk tube, the cocatalyst (methylaluminoxane—"MAO") was added. The "MAO" was purchased from Witco as a 1.78M solution in toluene. The Schlenk tube was purged with ethylene and the contents magnetically stirred and maintained under 1 bar ethylene for the duration of the polymerisation. After 60 minutes the polymerisation was terminated by addition of acidified methanol (50 ml HCl/2.5 liters methanol). The insoluble, solid, polyethylene was recovered by filtration, washed with methanol/water (1:4 v/v) and dried (vacuum oven at 50° C.). For Example 30, the produced polyethylene solution was dried over MgSO$_4$ and the solvent removed under vacuum to yield traces of a waxy material. The results of the polymerisation tests are shown in the following Table

TABLE

| Ex. | Catalyst/ mmol | Cocatalyst/ mmol | Fe:Al Ratio | Solid PE/g | Sol. PE | Activity/ gmmol$^{-1}$ bar$^{-1}$h$^{-1}$ |
|---|---|---|---|---|---|---|
| 30 | 0.02 | 8 | 1:400 | — | 0.04 | 2 |
| 31 | 0.008 | 3.2 | 1:400 | 1.01 | — | 130 |

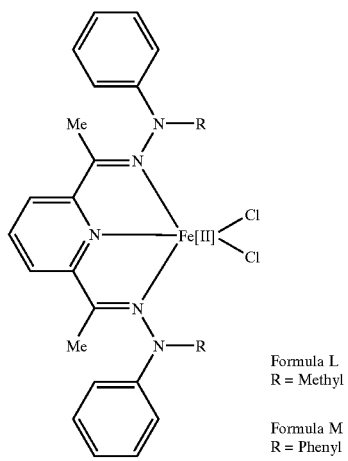

Formula L
R = Methyl

Formula M
R = Phenyl

Example 32

32.1—Preparation of a Supported Ziegler Catalyst Component

Silica (20 kg), grade ES 70 supplied by Crosfield, which had been dried at 800° C. for 5 hours in flowing nitrogen, was slurried in hexane (110 liters) and hexamethyldisilazane (30 moles), supplied by Fluka, was added with stirring at 50° C. Dry hexane (120 liters) was added with stirring, the solid allowed to settle, the supernatant liquid removed by decantation and further dry hexane (130 liters) was added with stirring. The hexane washing was repeated a further 3 times. Dibutylmagnesium (30 moles), supplied by FMC, was added and stirred for 1 hour at 50° C. Tertiary butyl chloride (60 moles) was added and stirred for 1 hour at 50° C. To this slurry was added an equimolar mixture of titanium tetrachloride (3 moles), and titanium tetra-n-propoxide (3 moles) with stirring at 50° C. for 2 hours, followed by 5 washings with dry hexane (130 liters). The slurry was dried under a flowing nitrogen stream to give a solid, silica supported Ziegler catalyst component.

32.2—Preparation of a Mixed Catalyst Containing a Ziegler Component and a Transition Metal Compound of the Present Invention A solution of methylaluminoxane ("MAO", 10.2 mmol) as a 10% wt solution in toluene, supplied by Witco, was added to a suspension of 2,6-diacetylpyridinebis(2,4,6-trimethylanil)FeCl$_2$ (0.07 mmol in 5 ml dry toluene), prepared as in Example 9, and the mixture shaken for 5 minutes. This solution was then added to 2.0 g of the silica supported Ziegler catalyst prepared above (Example 32.1), the mixture shaken for 2 hours at 20° C. and then the solvent removed under reduced pressure at 20° C. to yield the mixed catalyst as a free flowing powder.

32.3—Polymerisation of Ethylene/hexene Mixture Using the Mixed Catalyst

A 3 liter reactor equipped with a helical stirrer was heated to 95° C. for 1 hour with dry nitrogen flowing through. The temperature was reduced to 50° C. and dry sodium chloride (300 g) was then added with trimethylaluminium (TMA) solution (2 ml of 2 molar TMA in hexane) and the reactor heated at 85° C. for 2 hours. The reactor was purged with nitrogen, cooled to 50° C. and TMA solution (3ml of 2 molar TMA in hexane) added. The temperature was raised to 77° C. and hydrogen (0.5 bar) and ethylene (8 bar) added prior to the addition of 1-hexene (2.6 ml). Reaction was started by injection into the reactor of the mixed catalyst (0.20 g) prepared above. The temperature was maintained at 80° C. and ethylene added to maintain constant pressure. The gas phase was monitored by a mass spectrometer and hydrogen and 1-hexene added as necessary to maintain constant gas phase concentrations of these components. The polymerisation was carried out for 90 minutes. The polymer was washed with water to remove the sodium chloride, then with acidified methanol (50 ml HCl/2,5 liters methanol) and finally with water/ethanol (4:1 v/v ). The polymer was dried under vacuum, at 40° C. for 16 hours. 111 g of dried polymer was produced. The polymer had a broad molecular weight distribution (as determined by gel permeation chromatography. The polydispersity (Mw/Mn) was 28.5.

Example 33

33.1—Pre-impregnation of Support with Activator Compound

All the following operations were conducted under a nitrogen atmosphere unless stated. Silica (Crosfield grade ES70X) was heated under flowing nitrogen at 250° for 16 hours. A sample of this silica (2.5 g) was placed in a Schlenk tube and had 12.1 ml of 1.78M methylaluminoxane, MAO (supplied by Witco) added to it to form a slurry. The slurry was heated for 4 hours at 50° C. before being left for 10 days at room temperature. The supernatant liquid above the silica was removed and the silica/MAO washed three times with toluene (3×10 ml) at room temperature, removing the supernatant solution each time.

33.2—Supporting the Catalyst (2,6-diacetylpyridinebis(2,4,6 trimethyl anil) iron dichloride (0.101 g) (prepared as described in Example 9) was slurried in toluene (20 ml), at room temperature, and added to the silica/MAO. The mixture was occasionally shaken over a 1 hour period. The supernatant solution was removed and the silicaMAO/Fe complex was washed with toluene until the filtrate was colourless. The solid was dried under vacuum at 50° C.

33.3—Gas Phase Polymerisation of Ethylene

A 3 liter reactor was baked out under flowing nitrogen for at least 1 hour at 77° C. before sodium chloride (300 g, <1 mm diameter particles, predried under vacuum, 160° C., >4 hours) was added. The sodium chloride was employed merely as a standard "charge powder" for the gas phase polymerisation reactor. Trimethyl aluminium (3 ml, 2M in hexanes, supplied by Aldrich) was added to the reactor which was then closed. The alkyl aluminium was allowed to scavenge for poisons in the reactor for ½ hour before being vented by successive pressurising and purging the reactor with 4 bar of nitrogen. Ethylene (Grade 3.5, supplied by Air Products) was added to the reactor to give a pressure of 8 bar, at 77° C., prior to catalyst injection. The supported catalyst (0.215 g) prepared as described in Example 33.2 was injected into the reactor under nitrogen and the temperature then adjusted to 80° C. The polymerisation was allowed to continue for 5 hours before being terminated by purging the ethylene from the reactor, using nitrogen, and reducing the temperature to below 30° C. The polymer was washed with water to remove the sodium chloride, then with acidified methanol (50 ml HCl/2.5 liters methanol) and finally with water/ethanol (4:1 v/v). The polymer was dried under vacuum, at 40° C., for 16 hours. 161 g of dried polymer was produced.

Example 34
Polymerisation Catslyst Modified with a Neutral Lewis Base

The 2,6-diacetylpyridinebis(2,6-diisopropylanil)FeCl$_2$ complex prepared in Example 1 was tested in polymerisation of ethylene under the following standard conditions. To the iron complex (8 μmol) dissolved in dried toluene (10 ml) in a Schlenk tube, a solution of N,N-dimethylaniline in toluene (10 ml) then the cocatalyst (methylaluminoxane— 'MAO', 8 mmol of a 1.78M MAO solution in toluene, supplied by Witco, reference AL 5100/10 T) was added. The contents of the Schlenk were magnetically stirred and maintained under 1 bar ethylene for the duration of the polymerisation. After 60 minutes the produced polymer was washed with acidified methanol (50 ml HCl/2.5 liters methanol) and finally with water/ethanol (4:1 v/v). The polymer was dried under reduced pressure, at 40° C., for 16 hours. Several runs, using a variety of operating conditions were carried out and the polymerisation conditions are set out in the following Table.

| Run | DMA μmol | Fe/DMA Ratio | Activity | Mw | Mn | Mw/Mn |
|---|---|---|---|---|---|---|
| 34.1 | 8 | 1 | 890 | 790 | 660 | 1.2 |
| 34.2 | 80 | 10 | 617 | 1000 | 720 | 1.4 |
| 34.3 | 800 | 100 | 892 | 63000 | 4825 | 20.7 |
| C | — | — | 1030 | 89000 | 1100 | 77.8 |

Notes on the Table
DMA is N,N-dimethylaniline
Activity is expressed as g polymer mmol$^{-1}$ transition metal h$^{-1}$ bar$^{-1}$
C=Comparative Test using no DMA Examples 35 to 38

These illustrate the preparation of supported catalysts in accordance with the present invention and their use in the polymerisation of ethylene under "slurry" polymerisation conditions.

Example 35

35.1—Preparation of 2,6-diacetylpyridinebis(2,4,6 trimethyl anil) iron dichloride supported on MAO/silica Silica support material (grade ES70X supplied by Crosfield) was heated under flowing nitrogen at 250° C. for 16 hours . A sample of this silica was placed in a Schlenk tube and 12.1 ml of 1.78M methylaluminoxane ("MAO" supplied by Witco) was added to it to form a slurry. The slurry was heated for 4 hours at 50° C. before being left for 10 days at room temperature. The supernatant liquid above the silica was then removed and the silica/MAO washed 3 times with toluene (10 ml) at room temperature, removing the supernatant solution each time. 2,6-diacetylpyridinebis (2,4,6 trimethyl anil) iron dichloride complex (0.101 g) was slurried in toluene (20 ml), at room temperature, and added to the silica./MAO. The mixture was occasionally shaken over a 1 hour period. The supernatant solution was removed and the produced silica-supported MAO/Fe complex washed with toluene until the initial washings, which were light orange in colour, became clear and free from colour. The produced silica-supported catalyst solid was dried under vacuum at 50° C.

35.2—Polymerisation of Ethylene

A 1 liter reactor was heated under flowing nitrogen (2 liters/min) for 1 hour at 95° C. The reactor was cooled to 40° C. and 500 ml of isobutane added. The temperature of the reactor was raised to 80° C. and ethylene admitted to the reactor to give a partial pressure of 10 bar. The supported catalyst prepared in 35.1 above (0.201 g, slurried in 10 ml of toluene) was injected under nitrogen and the pressure increase in the reactor taken into account during control of the reactor pressure during the polymerisation test. The test was terminated after 1 hour and the polymer dried under vacuum at 40° C. 5.9 g of polymer was recovered. Analysis of the polymer by GPC indicated Mw and Mn to be 124000 and 15000 respectively.

35.3—Polymerisation of Ethylene

A 1 liter reactor was heated under flowing nitrogen for 3 hours at 80° C. The reactor was cooled to less than 30° C. and 500 ml of isobutane added. Trimethyl aluminium (3 ml of 2M in hexanes) was added to the reactor and this was then heated to 80° C. The pressure in the reactor increased to 13.8 bar and then ethylene was admitted to give a total pressure of 23.8 bar. The supported catalyst prepared in 35.1 above (0.201 g of the supported catalyst solid in toluene slurry) was injected into the reactor under nitrogen causing the reactor pressure to increase to 25.4 bar. The catalyst activity was slightly too high for the ethylene inlet flow to keep the pressure constant and this was therefore allowed to fall to 23.2 bar. The ethylene pressure present in the reactor for the majority of the polymerisation was estimated to be 7.8 bar. The test was terminated after 1.75 hours and the polymer washed with methanol/HCl (2.5 liters/50 ml), then water/ethanol (4:1 v/v) and dried under vacuum at 40° C. 166 g of dry polymer was recovered. Analysis of the polymer by GPC indicated Mw and Mn to be 182000 and 11000 respectively.

Example 36

36.1—Preparation of 2,6-diacetylpyridinebis(2,4,6 trimethvl anil) iron dichloride supported on MAO/silica A portion (about 1–1.5 g) of the supported catalyst prepared in Example 35.1 was washed with 5×10 ml aliquots of toluene at 100° C. The initial washings had a deep orange colour and this coloration became less with each subsequent washing until the final washing was clear of colour. The solid was dried under vacuum at 100° C. to provide free-flowing solid supported catalyst.

36.2—Polymerisation of Ethylene

A 1 liter reactor was heated under flowing nitrogen for 1 hour at 75° C. Trimethyl aluminium (3 ml of 2M in hexanes) was added to the reactor which was then cooled to 50° C. Isobutane (500 ml) was added to the reactor and the temperature increased to 76° C. The pressure in the reactor increased to 13 bar. Ethylene was admitted to the reactor to give 21 bar total pressure (8 bar ethylene). The supported catalyst prepared in 26.1 above ( 0.11 g in toluene slurry)

was injected into the reactor and the pressure increase taken into account during control of the reactor pressure during the test. The temperature was increased to 80° C. After 1 hour a further aliquot of the same catalyst was injected (0.22 g in hexane slurry) and the test continued for a further 3.5 hours. 25 g of polymer was recovered. Analysis of the polymer by GPC indicated Mw and Mn to be 343000 and 35000 respectively.

Example 37

37.1—Preparation of 2,6-diacetylpyridinebis(2,4,6 trimethyl anil) iron dichloride supported on MAO/silica Methyl aluminoxane (24 ml of 1.78M in toluene, supplied by Witco) was added to silica (5 g of grade ES70X supplied by Crosfield) which had been heated under flowing nitrogen at 250° C. The silica/MAO was heated at 80° C. for 1 hour before being washed toluene (5×10 ml aliquots). Half of the produced silica/MAO slurry, cooled to room temperature, was used for the next stage of the catalyst preparation (the other half was put aside for use in Example 38). 2,6-Diacetylpyridinebis(2,4,6 trimethyl anil) iron dichloride (73 mg) was slurried in toluene and transferred to the half-portion of silica/MAO/toluene and left to react for 2 hours with occasional mixing. The silica/MAO/Fe complex was washed with toluene (3×10 ml aliquots) at room temperature and then with hexane (2×10 ml aliquots) at room temperature to remove the toluene before finally being washed with hexane at 80° C. (3×10 ml aliquots). The produced supported catalyst solid was dried under vacuum at room temperature. The solid contained 0.107 weight % Fe.

37.2—Polymerisation of Ethylene

A 1 liter reactor was heated under flowing nitrogen for 1 hour at 80° C. The reactor was cooled to less than 30° C. and 500 ml of isobutane added. The reactor was heated to 77° C. and the pressure increased to 13.8 bar. Ethylene was added to give 21.8 bar total pressure (8 bar ethylene). Triisobutyl aluminium (5 ml of 1M in hexanes) was added to the reactor and after 20 minutes the supported catalyst prepared in 37.1 above (0. 14 g in hexane slurry) was injected into the reactor and the pressure increase taken into account during control of the reactor pressure during the test. The temperature was increased to 80° C. After 5 hours the polymerisation was terminated. 138 g of polymer was recovered. Analysis of the polymer by GPC indicated Mw and Mn to be 567000 and 53000 respectively. The produced polymer contained 1.02 ppm of Fe arising from the catalyst.

37.3—Polymerisation of Ethylene

A 1 liter reactor was heated under flowing nitrogen for 1 hour at 78° C. The reactor was cooled to less than 30° C. and 500 ml of isobutane added. Triisobutyl aluminium (3 ml of 1M in hexanes) was added to the reactor which was then heated to 78° C. and the pressure increased to 12.1 bar. Ethylene was added to give 32.0 bar total pressure (19.9 bar ethylene). The supported catalyst prepared in 37.1 above (0.0925 g, slurried in hexane) was injected into the reactor and the total pressure was controlled at 31.2 bar. The ethylene pressure during the polymerisation was estimated to be approximately 19.1 bar. Polymerisation was allowed to continue for 80 minutes. 181 g of polymer was recovered. Analysis of the polymer by GPC indicated Mw and Mn to be 595000 and 44000 respectively. The polymer contained 0.51 ppm of Fe arising from the catalyst.

37.4—Polymerisation of Ethylene

A 1 liter reactor was heated under flowing nitrogen for 1 hour at 80° C. before being cooled to less than 30° C. Triisobutyl aluminium (3 ml of IM in hexanes) was added to the reactor followed by 500 ml of isobutane. The reactor was heated to 78° C. and the pressure increased to 13.5 bar. Ethylene was added to give 17.6 bar total pressure (4.1 bar ethylene). The supported catalyst prepared in 37.1 above (0.15 g, slurried in hexane) was injected into the reactor. The ethylene pressure during the polymerisation was estimated to be approximately 4.7 bar. Polymerisation was allowed to continue for 80 minutes. 21 g of polymer was recovered. Analysis of the polymer by GPC indicated Mw and Mn to be 347000 and 26000 respectively.

Example 38

38.1—Preparation of 2,6-diacetylpyridinebis(2,6 diisopropyl anil) cobalt dichloride supported on MAO/silica The second half of the silica/MAO made in Example 37.1 was dried under vacuum. An aliquot of the dried silica/MAO (1 g) was placed in to a Schlenk tube and 2,6-diacetylpyridinebis(2,6 diisopropyl anil) cobalt dichloride (40 mg) added to this as a dry powder. Hexane (10 ml) was then added to the Schlenk tube and the cobalt complex and silicaO slurried together for 1 hour at room temperature. The mixture was dried under vacuum at room temperature to leave the produced supported catalyst as a dry, free flowing powder.

38.2—Polymerisation of Ethylene

A 1 liter reactor was heated under flowing nitrogen for 1 hour at 80° C. before being cooled to 30° C. Hexene (250 ml), triisobutyl aluminium (3 ml of 1M in hexanes) and 250 ml of isobutane were added to the reactor. The reactor was heated to 80° C. and the pressure increased to 7.1 bar. Ethylene was added to give 19.2 bar total pressure (12.1 bar ethylene). The supported catalyst prepared in above (0.245 g, slurried in hexane) was injected into the reactor and the pressure increase taken into account during control of the reactor pressure during the test. Polymerisation was allowed to continue for 330 minutes. 3.3 g of polymer was recovered. Analysis of the polymer by GPC indicated Mw=5300 and Mn=1500.

Example 39

Polymerisation of Ethylene in Slurry Phase Using a Supported Catalyst

A series of polymerisation tests was carried out using a catalyst based on a supported 2,6-diacetylpyridinebis(2,4,6 trimethyl anil) iron dichloride.

Example 39.1

A 1 liter reactor was heated under flowing nitrogen for 1 hour at 80° C. before being cooled to 30° C. Isobutane (500 ml) followed by triisobutyl aluminium (3 ml of 1M in hexanes) was added to the reactor. The reactor was heated to 78° C. and the pressure increased to 13.2 bar. Ethylene was added to give 26.2 bar total pressure. The catalyst of Example 37.1 (0.097 g, slurried in hexane) was injected into the reactor. The reactor pressure was controlled at 26.0 bar during the test (ethylene pressure estimated to be approximately 12.8 bar) and the temperature adjusted to 80° C. Polymerisation was allowed to continue for 60 minutes. 78 g of polymer was recovered. Analysis of the polymer by GPC indicated Mw and Mn to be 528000 and 40000 respectively.

Example 39.2

A 1 liter reactor was heated under flowing nitrogen for 1 hour at 80° C. before being cooled to 30° C. Isobutane (500ml) followed by triisobutyl aluminium (3 ml of 1M in hexanes) was added to the reactor. The reactor was heated to 78° C. and the pressure increased to 13.4 bar. Ethylene was added to give 21.2 bar total pressure. The catalyst of Example 37.1 (0.124 g, slurried in hexane) was injected into the reactor. The ethylene pressure was estimated to be approximately 8.1 bar during the polymerisation and the temperature adjusted to 80° C. Polymerisation was allowed to continue for 60 minutes. 47 g of polymer was recovered. Analysis of the polymer by GPC indicated Mw and Mn to be 376000 and 40000 respectively.

Example 39.3

A 1 liter reactor was heated under flowing nitrogen for 1 hour at 80° C. before being cooled to 30° C. Triisobutyl aluminium (3 ml of 1M in hexanes) was added to the reactor followed by 500 ml of isobutane. The reactor was heated to 78° C. and the pressure increased to 13.0 bar. Ethylene was added to give 26.0 bar total pressure. The catalyst of Example 37.1 (0.0966 g, slurried in hexane and 0.25 ml of NN dimethylaniline for 20 minutes) was injected into the reactor. The pressure in the reactor was allowed to fall to 22.5 bar to reduce the activity of the catalyst. The ethylene pressure in the reactor during the majority of the polymerisation was estimated to be 9.0 bar. Polymerisation was allowed to continue for 60 minutes. 88 g of polymer was recovered. Analysis of the polymer by GPC indicated Mw and Mn to be 430000 and 35000 respectively.

Example 39.4

A 1 liter reactor was heated under flowing nitrogen for 1 hour at 80° C. before being cooled to 30° C. Triisobutyl aluminium (3 ml of 1M in hexanes) was added to the reactor followed by 500 ml of isobutane. The reactor was heated to 78° C. and the pressure increased to 12.7 bar. Ethylene was added to give 14.7 bar total pressure. The catalyst of Example 37.1(0.104 g, slurried in hexane) was injected into the reactor. The ethylene pressure during the polymerisation was estimated to be approximately 2.2 bar. Polymerisation was allowed to continue for 60 minutes.4.8 g of polymer was recovered. Analysis of the polymer by GPC indicated Mw and Mn to be 340000 and 36000 respectively.

Example 40

40.1—Preparation of 2,6-diacetylpyridinebis (triphenylmethylimine)

To a solution of 2,6-diacetylpyridine (0.34 g; 2.1 mmol) in toluene (75 ml) was added triphenylmethylamine (1.20 g; 4.6 mmol.). After the addition of toluene sulphonic acid-monohydrate (0.05 g) the solution was refluxed overnight through a Dean-Stark apparatus. Upon cooling to room temperature the volatile components of the reaction mixture were removed in7 vacuo and the product crystallised from methanol. The product was filtered, washed with cold methanol and dried in a vacuum oven (30° C.) overnight. The yield was 1.02 g (33%).

40.2—Preparation 2,6-diacetylpyridinebis (triphenylmethylimine)FeBrz $FeBr_2$ (0.182 g; 0.84 mmol) was dissolved in hot n-butanol (30 ml) at 80° C. and solid 2,6-diacetylpyridinebis (triphenylmethylamine) (0.60 g; 0.93 mmol) was added in a number of portions. The reaction mixture turned purple. After stirring at 80° C. for 60 minutes the reaction was allowed to cool down to room temperature. Stirring was continued for 25 hours. The volatile components of the solution were removed under reduced pressure and the resultant purple solid washed with pentane (2×20 cm³) and dried int vacuo. The yield was 0.362 g (64% of theoretical).

40.3 Polymerisation Test

A polymerisation test was carried out using the following procedure. The 2,6-diacetylpyridinebis (triphenylmethylamine)$FeBr_2$ catalyst (0.008 millimoles) was added to a Schlenk tube, suspended in toluene (15 ml) and methylalumoxane cocatalyst ("MAO") was added to provide a mole ratio of MAO: Fe complex of 1000:1. The tube was purged with ethylene and the contents were mechanically stirred and maintained under 1 bar ethylene for the duration of the polymerisation. After ninety minutes the polymerisation was terminated by the addition of aqueous hydrogen chloride. The produced solid polyethylene was filtered off, washed with methanol and dried in a vacuum oven at 50° C. The yield of polyethylene was 0.185 g. This corresponds to a catalyst activity of 16 g $mmol^{-1}h^{-1}bar^{-1}$. No attempt was made to measure the quantity of any soluble polymer that may have been produced in this Example.

What is claimed is:

1. A process for the copolymerisation of polymerisable monomers comprising contacting two or more different polymerisable monomers selected from the group consisting of ethylene, propylene, 1-butene, 1-hexene, 4-methylpentene-1, octene, methyl methacrylate, methyl acrylate, butyl acrylate, acrylonitrile, vinyl acetate and styrene under polymerisation conditions with a polymerisation catalyst which comprises (1) a nitrogen-containing transition metal compound having the following Formula B, and (2) an activating quantity of activator compound selected from organoaluminium compounds and hydrocarbylboron compounds,

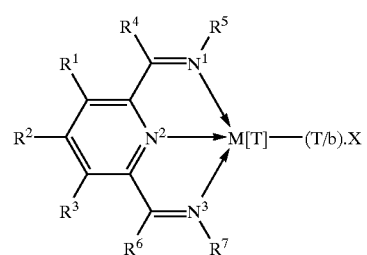

Formula B wherein M[T] is Fe[II], Fe[III], Co[I], Co[II], Co[III], Ru[II], Ru[III], Ru[IV], Mn[I], Mn[II], Mn[III], or Mn[IV]; X represents an atom or group covalently or ionically bonded to the transition metal M; T is the oxidation state of the transition metal M and b is the valency of the atom or group X; $R^1$, $R^2$, $R^3$, $R^4$, and $R^6$ are independently selected from hydrogen, halogen, hydrocarbyl, substituted hydrocarbyl, heterohydrocarbyl or substituted heterohydrocarbyl and such that (1):

when M is Fe, Co or Ru, $R^5$ and $R^7$ are independently selected from hydrogen, halogen, hydrocarbyl, substituted hydrocarbyl, heterohydrocarbyl or substituted heterohydrocarbyl; and when any two or more of $R^1$–$R^7$ are hydrocarbyl, substituted hydrocarbyl, heterohydrocarbyl or substituted heterohydrocarbyl, said two or more can be linked to form one or more cyclic substituents, or such that (2): when M is Fe, Co, Mn, or Ru then $R^5$ is represented by the group "P" and $R^7$ is represented by group "Q" as follows:

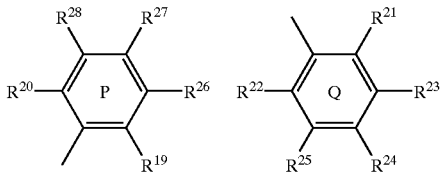

wherein $R^{19}$ to $R^{28}$ are independently selected from hydrogen, halogen, hydrocarbyl, substituted hydrocarbyl, heterohydrocarbyl or substituted heterohydrocarbyl; when any two or more of $R^1$ to $R^4$, $R^6$ and $R^{19}$ to $R^{28}$ are hydrocarbyl, substituted hydrocarbyl, heterohydrocarbyl or substituted heterohydrocarbyl, said two or more can be linked to form one or more cyclic substituents; with the proviso that at least one of $R^{19}$, $R^{20}$, $R^{21}$ and $R^{22}$ is hydrocarbyl, substituted hydrocarbyl, heterohydrocarbyl or substituted heterohydrocarbyl when neither of the ring systems P and Q forms part of a polyaromatic fused-ring system, or such that (3):

when M is Fe, Co, Mn or Ru, then $R^5$ is a group having the formula $-NR^{29}R^{30}$ and $R^7$ is a group having the formula $-NR^{31}R^{32}$, wherein $R^{29}$ to $R^{32}$ are independently selected from hydrogen, halogen, hydrocarbyl, substituted hydrocarbyl, heterohydrocarbyl or substituted heterohydrocarbyl; and when any two or more of $R^1$ to $R^4$, $R^6$ and $R^{29}$ to $R^{32}$ are hydrocarbyl, substituted hydrocarbyl, heterohydrocarbyl or substituted heterohydrocarbyl, said two or more can be linked to form one or more cyclic substituents.

2. A process as claimed in claim 1, wherein in the compound of Formula B M[T] is Ru[II], Ru[III], Ru[IV], Mn[I], Mn[II], Mn[III], or Mn[IV].

3. A process as claimed in claim 1 or 2, wherein the activator compound comprises a trialkylaluminium compound, an alumoxane, dimethylphenylammoniumtetra(phenyl)borate, trityltetra(phenyl)borate, triphenylboron, dimethylphenylammonium tetra(pentafluorophenyl)borate, sodium tetrakis[(bis-3,5-trifluoromethyl)phenyl]borate, H⁺(OEt₂)[bis-3,5-trifluoromethyl)phenyl]borate, trityltetra(pentafluorophenyl)borate or tris(pentafluorophenyl) boron.

4. A process as claimed in claim 1 wherein ethylene is copolymerised with another 1-olefin selected from propylene, 1-butene, 1-hexene, 4-methylpentene-1, and octene.

5. A process as claimed in claim 1, wherein gas is added to the polymerisation to control the average molecular weight of the produced polymer.

6. A process as claimed in claim 1, wherein the polymerisation temperature is in the range of 50 to 120° C. and the pressure is in the range 10 to 50 bar.

7. A process as claimed in claim 1, wherein the polymerisation conditions are solution phase, slurry phase or gas phase.

8. A process for the polymerisation of 1-olefins, comprising contacting the monomeric olefin under polymerisation conditions with a polymerisation catalyst which comprises (1) a nitrogen-containing transition metal compound having the following Formula B, and (2) an activating quantity of an activator compound selected from organoaluminium compounds and hydrocarbylboron compounds,

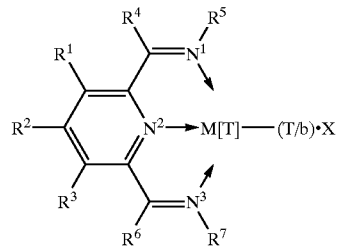

Formula B wherein M[T] is Fe[II], Fe[III], Co[I], Co[II], Co[III], Ru[II], Ru [III], Ru[IV], Mn[I], Mn[II], Mn[III], or Mn[IV]; X represents an atom or group covalently or ionically bonded to the transition metal M; T is the oxidation state of the transition metal M and b is the valency of the atom or group X; $R^1$, $R^2$, $R^3$, $R^4$, and $R^6$ are independently selected from hydrogen, halogen, hydrocarbyl, substituted hydrocarbyl, heterohydrocarbyl or substituted heterohydrocarbyl and such that (1):

when M is Fe, Co or Ru, $R^5$ and $R^7$ are independently selected from hydrogen, halogen, hydrocarbyl, substituted hydrocarbyl, heterohydrocarbyl or substituted heterohydrocarbyl; and when any two or more of $R^1$–$R^7$ are hydrocarbyl, substituted hydrocarbyl, heterohydrocarbyl or substituted heterohydrocarbyl, said two or more can be linked to form one or more cyclic substituents, or such that (2):

when M is Fe, Co, Mn or Ru, then $R^5$ is represented by the group "P" and $R^7$ is represented by the group "Q" as follows:

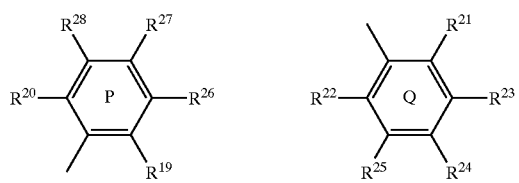

wherein $R^{19}$ to $R^{28}$ are independently selected from hydrogen, halogen, hydrocarbyl, substituted hydrocarbyl, heterohydrocarbyl or substituted heterohydrocarbyl; when any two or more of $R^1$ to $R^4$, $R^6$ and R19 to $R^{28}$ are hydrocarbyl, substituted hydrocarbyl, heterohydrocarbyl or substituted heterohydrocarbyl, said two or more can be linked to form one or more cyclic substituents; with the proviso that at least one of $R^{19}$, $R^{20}$ $R^{21}$ and $R^{22}$ is hydrocarbyl, substituted hydrocarbyl, heterohydrocarbyl or substituted heterohydrocarbyl when neither of the ring systems P and Q forms part of a polyaromatic fused-ring system, or such that (3):

when M is Fe, Co, Mn or Ru, then $R^5$ is a group having the formula $-NR^{29}R^{30}$ and $R^7$ is a group having the formula $-NR^{31}R^{32}$, wherein $R^{29}$ to $R^{32}$ are independently selected from hydrogen, halogen, hydrocarbyl, substituted hydrocarbyl, heterohydrocarbyl or substituted heterohydrocarbyl, and when any two or more of $R^1$ to $R^4$, $R^6$ and $R^{29}$ to $R^{32}$ are hydrocarbyl, substituted hydrocarbyl, heterohydrocarbyl or substituted heterohydrocarbyl, said two or more can be linked to form one or more cyclic substituents, wherein the polymerisation conditions are gas phase fluidised bed conditions; and wherein the catalyst, or one or more of the components employed to form the catalyst, are introduced into the polymerisation reaction zone in liquid form, and the liquid containing the component(s) is sprayed as fine droplets into the polymerisation zone.

9. A process as claimed in claim 1 wherein the polymerisation is conducted under gas phase fluidised bed conditions.

10. A process as claimed in claim 9, wherein volatile liquid is fed to the fluidised bed under conditions such that the liquid evaporates in the bed thereby absorbing additional heat of polymerisation from the bed.

11. A process as claimed in claim 10, wherein the volatile liquid is condensed out in a heat exchanger.

12. A process as claimed in claim 11, wherein said volatile liquid is separated from the recycle gas.

13. A process as claimed in claim 12, wherein said volatile liquid is sprayed into the bed.

14. A process as claimed in claim 11, wherein said volatile liquid is recycled to the bed with recycle gas.

15. A process as claimed in claims 9, wherein the fluidising gas for the fluidised bed contains an inert gas.

16. A process as claimed in claim 15, wherein the inert gas comprises nitrogen or pentane.

17. A process as claimed in claim 9, wherein the catalyst, or one or more of the components employed to form the catalyst, are introduced into the polymerisation reaction zone in liquid form, and the liquid containing the component (s) is sprayed as fine droplets into the polymerisation zone.

18. A process for the polymerisation of polymerisable monomers comprising contacting a polymerisable monomer under polymerisation conditions with a polymerisation catalyst comprising
   (1) a nitrogen-containing transition metal compound having the following Formula B, and
   (2) an activating quantity of an activator compound selected from organoaluminium compounds and hydrocarbylboron compounds,

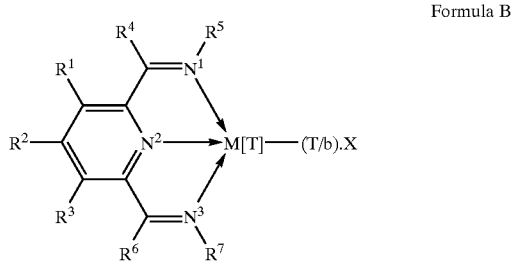

Formula B wherein M[T] is Ru[II], Ru[III], Ru[IV], Mn[I], Mn[II], Mn[III], or Mn[IV]; X represents an atom or group covalently or ionically bonded to the transition metal M; T is the oxidation state of the transition metal M and b is the valency of the atom or group X; $R^1$, $R^2$, $R^3$, $R^4$, and $R^6$ are independently selected from hydrogen, halogen, hydrocarbyl, substituted hydrocarbyl, heterohydrocarbyl or substituted heterohydrocarbyl and such that (1):

when M is Ru, $R^5$ and $R^7$ are independently selected from hydrogen, halogen, hydrocarbyl, substituted hydrocarbyl, heterohydrocarbyl or substituted heterohydrocarbyl; and when any two or more of $R^1$–$R^7$ are hydrocarbyl, substituted hydrocarbyl, heterohydrocarbyl or substituted heterohydrocarbyl, said two or more can be linked to form one or more cyclic substituents, or such that (2):

when M is Mn or Ru, then $R^5$ is represented by the group "P" and $R^7$ is represented by the group "Q" as follows:

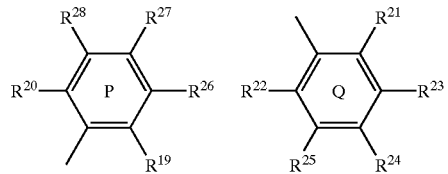

wherein $R^{19}$ to $R^{28}$ are independently selected from hydrogen, halogen, hydrocarbyl, substituted hydrocarbyl, heterohydrocarbyl or substituted heterohydrocarbyl; when any two or more of $R^1$ to $R^4$, $R^6$ and $R^{19}$ to $R^{28}$ are hydrocarbyl, substituted hydrocarbyl, heterohydrocarbyl or substituted heterohydrocarbyl, said two or more can be linked to form one or more cyclic substituents; with the proviso that at least one of $R^{19}$, $R^{20}$, $R^{21}$ and $R^{22}$ is hydrocarbyl, substituted hydrocarbyl, heterohydrocarbyl or substituted heterohydrocarbyl when neither of the ring systems P and Q forms part of a polyaromatic fused-ring system, or such that (3)

when M is Mn or Ru, then $R^5$ is a group having the formula —$NR^{29}R^{30}$ and $R^7$ is a group having the formula —$NR^{31}R^{32}$, wherein $R^{29}$ to $R^{32}$ are independently selected from hydrogen, halogen, hydrocarbyl, substituted hydrocarbyl, heterohydrocarbyl or substituted heterohydrocarbyl; when any two or more of $R^1$ to $R^4$, $R^6$ and $R^{29}$ to $R^{32}$ are hydrocarbyl, substituted hydrocarbyl, heterohydrocarbyl or substituted heterohydrocarbyl, said two or more can be linked to form one or more cyclic substituents.

19. A process as claimed in claim 18, wherein the monomer is ethylene, propylene, butene, hexene, methyl methacrylate, methyl acrylate, butyl acrylate, acrylonitrile, vinyl acetate or styrene.

20. A process as claimed in claim 18, wherein hydrogen gas is ad to the polymerisation to control the average molecular weight of the produced polymer.

21. A process as claimed in claim 18, wherein the polymerisation temperature is in the range of 50 to 120° C. and the pressure is in the range 10 to 50 bar.

22. A process as claimed in claim 18, wherein the polymerisation conditions are solution phase, slurry phase or gas phase.

23. A process for the polymerisation of 1-olefins, comprising contacting the monomeric olefin under gas phase fluidised bed polymerisation conditions with a polymerisation catalyst which comprises
   (1) a nitrogen-containing transition metal compound having the following Formula B, and
   (2) an activating quantity of an activator compound selected from organoaluminium compounds and hydrocarbylboron compounds,

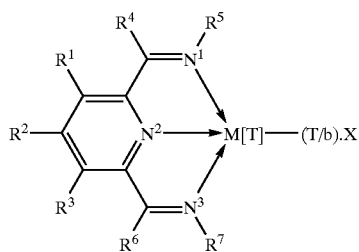

Formula B wherein M[T] is Fe[II], Fe[III], Co[I], Co[II], Co[III], Ru[II], Ru[III], Ru[IV], Mn[I], Mn[II], Mn[III], or Mn[IV]; X represents an atom or group covalently or ionically bonded to the transition metal M; T is the oxidation state of the transition metal M and b is the valency of the atom or group X; $R^1$, $R^2$, $R^3$, $R^4$, and $R^6$ are independently selected from hydrogen, halogen, hydrocarbyl, substituted hydrocarbyl, heterohydrocarbyl or substituted heterohydrocarbyl and such that (1):

when M is Fe, Co or Ru, $R^5$ and $R^7$ are independently selected from hydrogen, halogen, hydrocarbyl, substituted hydrocarbyl, heterohydrocarbyl or substituted heterohydrocarbyl; and when any two or more of $R^1$–$R^7$ are hydrocarbyl, substituted hydrocarbyl, heterohydrocarbyl or substituted heterohydrocarbyl, said two or more can be linked to form one or more cyclic substituents, or such that (2):

when M is Fe, Co, Mn or Ru, then $R^5$ is represented by the group "P" and $R^7$ is represented by the group "Q" as follows:

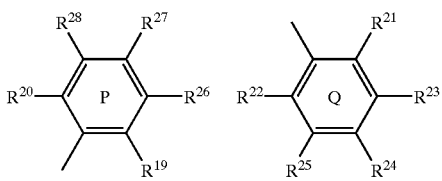

wherein $R^{19}$ to $R^{28}$ are independently selected from hydrogen, halogen, hydrocarbyl, substituted hydrocarbyl, heterohydrocarbyl or substituted heterohydrocarbyl; when any two or more of $R^1$ to $R^4$, $R^6$ and $R^{19}$ to $R^{28}$ are hydrocarbyl, substituted hydrocarbyl, heterohydrocarbyl or substituted heterohydrocarbyl, said two or more can be linked to form one or more cyclic substituents; with the proviso that at least one of $R^{19}$, $R^{20}$, $R^{21}$ and $R^{22}$ is hydrocarbyl, substituted hydrocarbyl, heterohydrocarbyl or substituted heterohydrocarbyl when neither of the ring systems P and Q forms part of a polyaromatic fused-ring system, or such that (3)

when M is Fe, Co, Mn or Ru, then $R^5$ is a group having the formula —$NR^{29}R^{30}$ and $R^7$ is a group having the formula —$NR^{31}R^{32}$, wherein $R^{29}$ to $R^{32}$ are independently selected from hydrogen, halogen, hydrocarbyl, substituted hydrocarbyl, heterohydrocarbyl or substituted heterohydrocarbyl; and when any two or more of $R^1$ to $R^4$, $R^6$ and $R^{29}$ to $R^{32}$ are hydrocarbyl, substituted hydrocarbyl, heterohydrocarbyl or substituted heterohydrocarbyl, said two or more can be linked to form one or more cyclic substituents, wherein hydrogen gas is added to the polymerisation to control the average molecular weight of the produced polymer.

24. A process as claimed in claim 23, wherein the polymerisation temperature is in the range of 50 to 120° C. and the pressure is in the range 10 to 50 bar.

25. A process as claimed in claim 23, wherein volatile liquid is fed to the fluidised bed under conditions such that the liquid evaporates in the bed thereby absorbing additional heat of polymerisation from the bed.

26. A process as claimed in claim 25, wherein the volatile liquid is condensed out in a heat exchanger.

27. A process as claimed in claim 26, wherein said volatile liquid is separated from the recycle gas.

28. A process as claimed in claim 27, wherein said volatile liquid is sprayed into the bed.

29. A process as claimed in claim 26, wherein said volatile liquid is recycled to the bed with recycle gas.

30. A process as claimed in claim 23, wherein the fluidising gas for the fluidised bed contains an inert gas.

31. A process as claimed in claim 20, wherein the inert gas comprises nitrogen or pentane.

32. A process as claimed in claim 23, wherein the catalyst, or one or more of the components employed to form the catalyst, are introduced into the polymerisation reaction zone in liquid form, and the liquid containing the component(s) is sprayed as fine droplets into the polymerisation zone.

33. The process of any one of claims 1, 12, or 23 wherein the catalyst is supported on a support material.

34. The process of claim 23, wherein the support material is silica, alumina, zirconia, a polymer, or a prepolymer.

* * * * *

UNITED STATES PATENT AND TRADEMARK OFFICE
CERTIFICATE OF CORRECTION

PATENT NO. : 6,451,939 B1 Page 1 of 1
DATED : September 17, 2002
INVENTOR(S) : George Johan Peter Britovsek et al.

It is certified that error appears in the above-identified patent and that said Letters Patent is hereby corrected as shown below:

Column 44,
Line 56, "tonically" should read -- ionically --.

Column 45,
Line 4, after "Ru" insert a comma.
Line 5, after "by" (second occurrence) insert -- the --.
Line 50, after "claim 1" insert comma.
Line 54, after "wherein" insert -- hydrogen --.

Column 46,
Formula B, line 10, "·X" should read -- .X --.
Line 52, "R19" should read -- $R^{19}$ --.
Line 56, after "$R^{20}$" insert a comma.

Column 48,
Line 49, "ad" should read -- added --.

Column 50,
Line 38, "claim 20" should read -- claim 30 --.
Line 45, "12" should read -- 18 --.
Line 47, "claim 23" should read -- claim 33 --.

Signed and Sealed this

Fourth Day of February, 2003

JAMES E. ROGAN
*Director of the United States Patent and Trademark Office*